United States Patent
Wen et al.

(10) Patent No.: US 12,054,411 B2
(45) Date of Patent: *Aug. 6, 2024

(54) SYSTEMS AND METHODS FOR REDUCING TOTAL DISSOLVED SOLIDS (TDS) IN WASTEWATER BY AN ALGAL BIOFILM TREATMENT

(71) Applicants: Iowa State University Research Foundation, Inc., Ames, IA (US); Metropolitan Water Reclamation District of Greater Chicago, Chicago, OH (US)

(72) Inventors: Zhiyou Wen, Ames, IA (US); Juan Peng, Ames, IA (US); Martin A. Gross, Ames, IA (US); Kuldip Kumar, Chicago, IL (US); Thomas Kunetz, Chicago, IL (US)

(73) Assignees: Iowa State University Research Foundation, Inc., Ames, IA (US); Metropolitan Water Reclamation District of Greater Chicago, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/199,051

(22) Filed: May 18, 2023

(65) Prior Publication Data
US 2023/0348303 A1 Nov. 2, 2023

Related U.S. Application Data

(63) Continuation of application No. 16/748,211, filed on Jan. 21, 2020, now Pat. No. 11,691,902.
(Continued)

(51) Int. Cl.
*C02F 3/08* (2023.01)
*C02F 1/66* (2023.01)

(52) U.S. Cl.
CPC . *C02F 3/08* (2013.01); *C02F 1/66* (2013.01)

(58) Field of Classification Search
CPC ........ C02F 3/08; C02F 1/66; C02F 2103/007; C02F 3/10; C02F 2203/006;
(Continued)

(56) References Cited

U.S. PATENT DOCUMENTS

| | | | |
|---|---|---|---|
| 3,565,797 | A | 2/1971 | Gresham |
| 3,598,726 | A | 8/1971 | Welch |

(Continued)

FOREIGN PATENT DOCUMENTS

| | | |
|---|---|---|
| CN | 103289887 A | 9/2013 |
| WO | WO 2010/011320 A1 | 1/2010 |
| WO | WO 2010/030953 A1 | 3/2010 |

OTHER PUBLICATIONS

ABIOTIC_Definition_NPL.pdf (Year 2022).
(Continued)

*Primary Examiner* — Ekandra S. Miller-Cruz
(74) *Attorney, Agent, or Firm* — Frost Brown Todd LLP; Vance V. VanDrake, III; Alexander J. Johnson

(57) ABSTRACT

A system for reducing total dissolved solids in wastewater can include a vertical reactor that can include a flexible sheet material, where the flexible sheet material can be configured to facilitate the growth and attachment of an algal biofilm. The vertical reactor can include a shaft, where the shaft can be associated with and can support the flexible sheet material, and a drive motor, where the drive motor can be coupled with the shaft such that the flexible sheet material can be selectively actuated. The system can include a fluid reservoir containing a portion of wastewater through which the flexible sheet material is configured to pass as well as a stressor operably configured to stimulate the algae to produce an extracellular polymeric substance. A method of reducing
(Continued)

total dissolved solids in wastewater includes moving an algal biofilm through the wastewater and moving the algal biofilm through a gas.

18 Claims, 25 Drawing Sheets

Related U.S. Application Data

(60) Provisional application No. 62/795,122, filed on Jan. 22, 2019.

(58) Field of Classification Search
CPC ............ C02F 2209/10; C02F 2301/028; C02F 2101/10; C02F 2101/101; C02F 3/322; Y02W 10/37; Y02W 10/10
See application file for complete search history.

(56) References Cited

U.S. PATENT DOCUMENTS

| | | | |
|---|---|---|---|
| 4,324,068 A | | 4/1982 | Myron |
| 4,554,390 A | | 11/1985 | Curtain et al. |
| 5,227,067 A | * | 7/1993 | Runyon .................. C02F 3/006 210/170.09 |
| 5,447,629 A | | 9/1995 | Chaumont |
| 5,647,983 A | | 7/1997 | Limcaco |
| 6,158,386 A | | 12/2000 | Limcaco |
| 6,203,700 B1 | | 3/2001 | Rose |
| 6,667,171 B2 | | 12/2003 | Bayless et al. |
| 6,794,184 B1 | | 9/2004 | Mohr et al. |
| 8,372,631 B2 | | 2/2013 | Shepherd |
| 8,377,687 B2 | | 2/2013 | Shepherd |
| 8,658,414 B2 | | 2/2014 | Hornung |
| 8,920,810 B2 | | 12/2014 | Adey et al. |
| 9,932,549 B2 | | 4/2018 | Gross et al. |
| 10,125,341 B2 | | 11/2018 | Wen et al. |
| 10,570,359 B2 | | 2/2020 | Gross et al. |
| 11,691,902 B2 | | 7/2023 | Wen et al. |
| 2008/0135474 A1 | | 6/2008 | Limcaco |
| 2009/0230040 A1 | | 9/2009 | Limcaco |
| 2010/0144017 A1 | | 6/2010 | Shepherd |
| 2010/0224574 A1 | | 9/2010 | Youngs et al. |
| 2010/0267122 A1 | | 10/2010 | Chinnasamy et al. |
| 2011/0070632 A1 | | 3/2011 | Katoch et al. |
| 2011/0217764 A1 | | 9/2011 | Christenson et al. |
| 2011/0258915 A1 | | 10/2011 | Subhadra |
| 2011/0263886 A1 | | 10/2011 | Kale |
| 2011/0283608 A1 | | 11/2011 | Patel et al. |
| 2011/0312062 A1 | | 12/2011 | Nordvik et al. |
| 2012/0018373 A1 | | 1/2012 | Jones et al. |
| 2012/0152832 A1 | | 6/2012 | Johnson et al. |
| 2012/0252105 A1 | | 10/2012 | Ahrens et al. |
| 2013/0269244 A1 | | 10/2013 | Jovine |
| 2014/0273171 A1 | | 9/2014 | Gross et al. |
| 2014/0273174 A1 | | 9/2014 | Gross et al. |
| 2015/0305330 A1 | | 10/2015 | Alper |
| 2016/0039693 A1 | | 2/2016 | Kuehnle et al. |
| 2016/0075989 A1 | | 3/2016 | Carberry et al. |
| 2016/0090317 A1 | | 3/2016 | Ju et al. |
| 2017/0233272 A1 | | 8/2017 | Chidambaran et al. |
| 2017/0321181 A1 | | 11/2017 | Hazlebeck et al. |
| 2018/0171275 A1 | | 6/2018 | Wen et al. |
| 2018/0201887 A1 | | 7/2018 | Gross et al. |
| 2019/0248688 A1 | | 8/2019 | Wen et al. |
| 2020/0022384 A1 | | 1/2020 | Gross et al. |
| 2020/0024559 A1 | | 1/2020 | Gross et al. |
| 2020/0048122 A1 | | 2/2020 | Gross et al. |
| 2020/0123482 A1 | | 4/2020 | Gross et al. |

OTHER PUBLICATIONS

Bitog et al.; "Application of Computational Fluid Dynamics for Modeling and Designing Photobioreactors for Microalgae Production: A review," Computers and Electronics in Agriculture (2011), 76:131-147, Jan. 24, 2011.

Borowitzka, The "stress" concept in microalgal biology—homeostasis, acclimation and adaption (Year: 2018).

Christenson et al., "Rotating Algal Biofilm Reactor and Spool Harvester for Wastewater Treatment with Biofuels By-Products", Biotechnology and Bioengineering, DOI 10.1002/bit.24451 (2012) Wiley Periodicals, Inc. Jan. 20, 2012.

Peng, Juan et al.; "Removal of Total Dissolved Solids from wastewater Using a Revolving Algal Reactor," Water Environment Research 92 (2020), pp. 766-778, Water Environment Federation.

Peng et al., Removal of Total Dissolved Solids from Wastewater Using a Revolving Algal Biofilm Reactor, Water Environment Research, Nov. 12, 2019 [retrieved on Mar. 1, 2020]. Retrieved from the Internet: <URL: https://onlinelibrary.wiley.com/doi/abs/10.1002/wer.1273>. Abstract.

Johnson, et al., "Development of an Attached Microalgal Growth System for Biofuel Production", Applied Microbiology and Biotechnology (2010), 85:525-534, Jul. 7, 2009.

Zhao, Xuefel et al.; Evaluation of Revolving algae Biofilm Reactors for Nutrients and Metals Removal from Sludge Thickening Supernatant in a Municipal Wastewater Treatment Facility, Water Research 143 (2018), pp. 467-478, Elsevier Ltd.

Extended European Search Report from corresponding EP Application No. 20744373, European Patent Office, Nov. 7, 2022, 10 pages.

International Search Report for International Application No. PCT/US2014/029618, mailed Aug. 21, 2014.

International Search Report and Written Opinion of the International Searching Authority for International Patent Application No. PCT/US2020/014393 dated as mailed on Mar. 25, 2020; 10 pages.

Written Opinion of the International Searching Authority for International Application No. PCT/US2014/029618, mailed Aug. 21, 2014, 4 pages.

Xiao et al. "Overview of microalgal extracellular polymeric substances (EPS) and their applications." Biotechnology advances 34.7 (2016): 1225-1244.

Office Action dated Oct. 25, 2023 for CA Patent Application No. 3,126,942, 5 pages.

U.S. Appl. No. 18/199,061, filed May 18, 2023.

\* cited by examiner

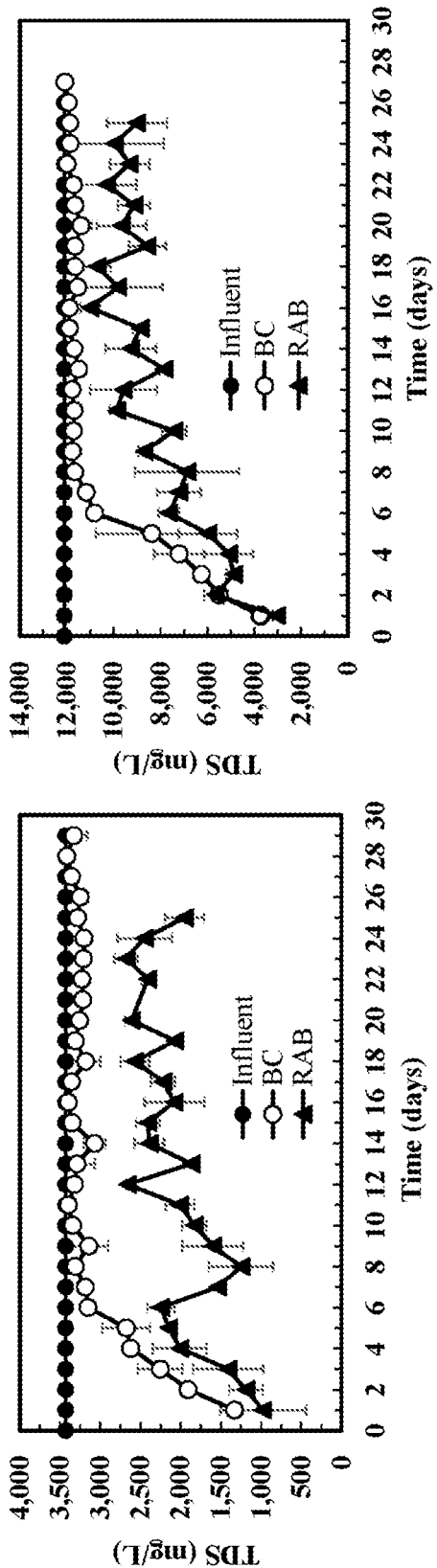
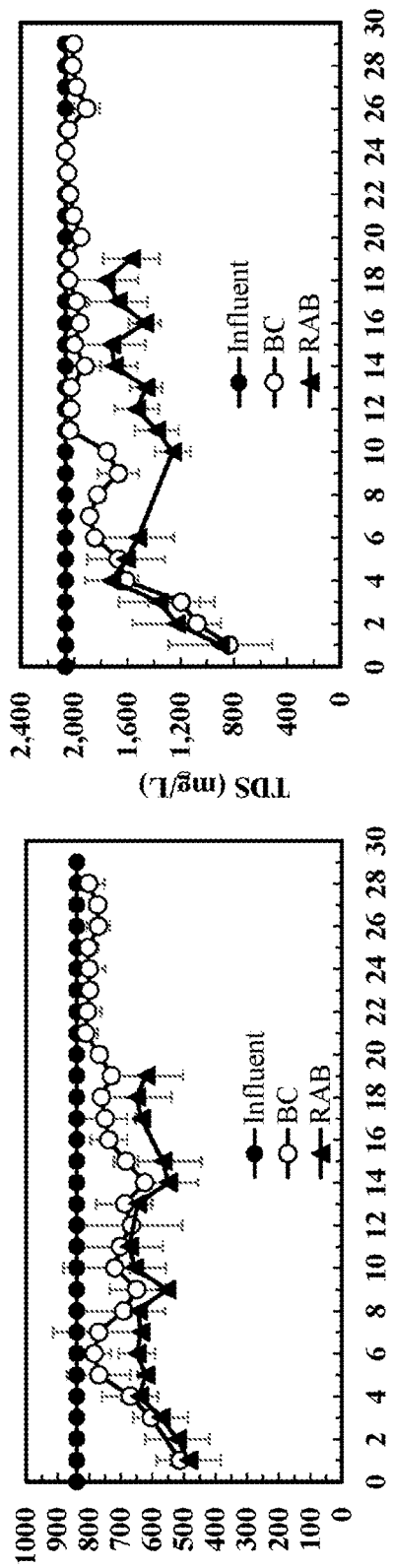
FIG. 23A
FIG. 23B
FIG. 23C
FIG. 23D

SYSTEMS AND METHODS FOR REDUCING TOTAL DISSOLVED SOLIDS (TDS) IN WASTEWATER BY AN ALGAL BIOFILM TREATMENT

REFERENCE TO RELATED APPLICATIONS

The present application is a continuation application of U.S. patent application Ser. No. 16/748,211, filed Jan. 21, 2020 which claims the priority benefit of U.S. provisional patent application Ser. No. 62/795,122, filed Jan. 22, 2019, and hereby incorporates the same application herein by reference in its entirety.

TECHNICAL FIELD

Embodiments of the technology relate, in general, to biofilm technology, and in particular to the application of a revolving algal biofilm photobioreactor (RABP) for removal of Total Dissolved Solids (TDS).

BACKGROUND

Total dissolved solids (TDS) is generally comprised of inorganic salts (e.g., chloride, calcium, magnesium, potassium, sodium, bicarbonates, and sulfates) and organic matters dissolved in water. Natural waterbodies commonly contain a certain level of TDS, but human activities such as agriculture, water use and treatment, urbanization, de-icing salt applications, and mining can significantly exacerbate the TDS level in surface and ground waters. This excess TDS can be toxic to aquatic life. In the U.S., TDS discharge limit for wastewater has been increasingly implemented at state levels. Various methods such as reverse osmosis (RO), distillation, and membrane filtration have been developed to reduce/remove TDS from various water streams. However, most existing methods are not cost-effective and/or environmental friendly. For example, distillation can produce low conductivity water but the process is very energy-intensive due to the large amount of latent heat required. A need exists for improved methods of TDS removal that are cost-effective and environmentally friendly.

BRIEF DESCRIPTION OF THE DRAWINGS

The present disclosure will be more readily understood from a detailed description of some example embodiments taken in conjunction with the following figures:

FIG. 23A depicts the concentration of TDS in the influent and effluent during the continuous operation of the RAB and BC reactors fed with a wastewater (WW) source of low-TDS industrial WW.

FIG. 23B depicts the concentration of TDS in the influent and effluent during the continuous operation of the RAB and BC reactors fed with a wastewater (WW) source of high-TDS industrial WW.

FIG. 23C depicts the concentration of TDS in the influent and effluent during the continuous operation of the RAB and BC reactors fed with a wastewater (WW) source of AMES WW.

FIG. 23D depicts the concentration of TDS in the influent and effluent during the continuous operation of the RAB and BC reactors fed with a wastewater (WW) source of AMES WW+NaCl.

SUMMARY

Figure 1:
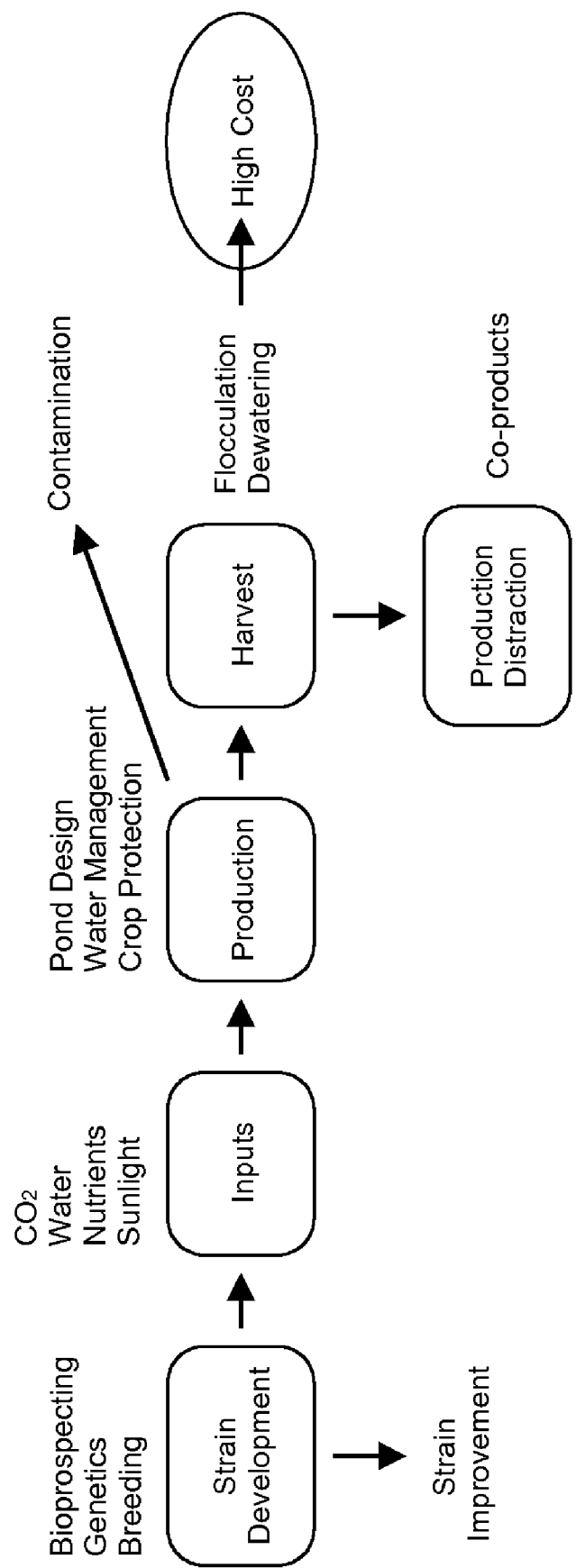
FIG. 1 depicts a flow chart illustrating the methodology generally associated with algae harvesting.

A method of reducing total dissolved solids (TDS) in wastewater can include providing an algal biofilm, the algal biofilm comprising a material configured for the growth and attachment of algae, providing a fluid reservoir containing a portion of wastewater fluid, and moving the algal biofilm through the portion of wastewater fluid in the fluid reservoir. The method can further include providing a stressor to algae in the algal biofilm to stimulate production of an extracellular polymeric substance and removing a portion of total dissolved solids in the portion of wastewater fluid with the extracellular polymeric substance.

An algal growth system for reducing total dissolved solids (TDS) in wastewater can include a vertical reactor comprising a flexible sheet material, the flexible sheet material being configured to facilitate the growth and attachment of an algal biofilm, a shaft, wherein the shaft is associated with and supports the flexible sheet material, and a drive motor, the drive motor being coupled with the shaft such that the flexible sheet material is selectively actuated. The system can also include a fluid reservoir, the fluid reservoir containing a portion of wastewater containing an amount of total dissolved solids, wherein the flexible sheet material is configured to pass through the fluid reservoir during operation of the algal growth system, and a stressor, wherein the stressor is operably configured to stimulate algae in the algal biofilm to produce an extracellular polymeric substance.

A method of reducing total dissolved solids (TDS) in wastewater can include providing an algal growth system comprising a vertical reactor comprising a flexible sheet material, the flexible sheet material being configured to facilitate the growth and attachment of algae, a shaft, wherein the shaft is associated with and supports the flexible sheet material, and a drive motor, the drive motor being coupled with the shaft such that the flexible sheet material is selectively actuated. The system can also include a fluid reservoir, wherein the flexible sheet material is configured to pass through the fluid reservoir during operation of the algal growth system, the vertical reactor being positioned at least partially within the fluid reservoir, and a portion of wastewater, wherein the portion of wastewater is retained within the fluid reservoir and includes an amount of total dissolved solids. The method can further include rotating the flexible sheet material of the algal growth system through the portion of wastewater retained in the fluid reservoir in a first liquid phase, rotating the flexible sheet material of the algal growth system through a gas in a second gas phase to stimulate production of an extracellular polymeric substance, and harvesting the algae from the flexible sheet material. Stimulating the production of the extracellular polymeric substance reduces the amount of total dissolved solids in the portion of wastewater.

DETAILED DESCRIPTION

Various non-limiting embodiments of the present disclosure will now be described to provide an overall understanding of the principles of the structure, function, and use of the systems and processes disclosed herein. One or more examples of these non-limiting embodiments are illustrated in the accompanying drawings. Those of ordinary skill in the art will understand that systems and methods specifically described herein and illustrated in the accompanying drawings are non-limiting embodiments. The features illustrated or described in connection with one non-limiting embodiment may be combined with the features of other non-limiting embodiments. Such modifications and variations are intended to be included within the scope of the present disclosure.

Reference throughout the specification to "various embodiments," "some embodiments," "one embodiment," "some example embodiments," "one example embodiment," or "an embodiment" means that a particular feature, structure, or characteristic described in connection with any embodiment is included in at least one embodiment. Thus, appearances of the phrases "in various embodiments," "in some embodiments," "in one embodiment," "some example embodiments," "one example embodiment," or "in an embodiment" in places throughout the specification are not necessarily all referring to the same embodiment. Furthermore, the particular features, structures or characteristics may be combined in any suitable manner in one or more embodiments.

Traditionally, algae are grown in open raceway ponds or enclosed photobioreactors, where algae cells are in suspension and are harvested through sedimentation, filtration, or centrifugation. Due to the light penetration problem caused by mutual shading of suspended algal cells, the algal growth in suspension is often limited by light availability. Also, due to the small size (3-30 μm) of algae cells and the dilute algae concentration (<1% w/v), gravity sedimentation of suspended cells often takes a long time in a large footprint settling pond. Filtration of algal cells from the culture broth can result in filter fouling. Centrifugation can achieve high harvest efficiency; however, the capital investment and operational cost for a centrifugation system can be prohibitively expensive. Due to these drawbacks, an alternative method for growing and harvesting algae biomass may be advantageous.

Described herein are example embodiments of revolving algal biofilm photobioreactor systems and methods that can enhance cell growth and simplify biomass harvesting. In one example embodiment, systems and methods can provide cost effective harvesting of algae biomass. In some embodiments, systems and methods can be used to produce algae for biofuel feedstock, and aquacultural feed, and nutraceuticals. In some embodiments, algal cells can be attached to a material that can be rotated between a nutrient-rich liquid phase and a gaseous phase, such as a carbon dioxide rich gaseous phase, such that alternative absorption of nutrients and the gas can occur. The algal cells can be harvested by scraping from the surface to which they are attached, which can eliminate harvest procedures commonly used in suspension cultivation systems, such as sedimentation, flocculation, floatation, and/or centrifugation. It will be appreciated that systems and methods described herein can be combined with sedimentation, centrifugation, or any other suitable processes.

The examples discussed herein are examples only and are provided to assist in the explanation of the apparatuses, devices, systems and methods described herein. None of the features or components shown in the drawings or discussed below should be taken as mandatory for any specific implementation of any of the apparatuses, devices, systems or methods unless specifically designated as mandatory. For ease of reading and clarity, certain components, modules, or methods may be described solely in connection with a specific figure. Any failure to specifically describe a combination or sub-combination of components should not be understood as an indication that any combination or sub-combination is not possible. Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

Example embodiments described herein can mitigate air and water pollution while delivering high value bio-based products such as bio-fuels, nutraceuticals, and animal feeds from microalgae. Example embodiments of RAB technology can play a beneficial role in creating an algal culture system that can economically produce algae biomass for, for example, biofuels, nutraceuticals, and animal feeds. Microalgae may have a significant impact in the renewable transportation fuels sector. Example embodiments can grow microalgae that can be used in biofuel production with a low harvest cost. Algae, if produced economically, may also serve as a primary feed source for nutraceuticals and aqua feeds production.

Referring to FIG. 1, low biomass productivity and high cost of algae production can still be the major limitation in industrial scale operation. Example embodiments described herein may minimize such costs associated with the growth and harvesting of algal cells from an aqueous culture system.

Generally, research on algae cultivation is done using suspended algae culture. This culture method can have drawbacks including low biomass yield and productivity and low efficiency of harvesting the algal cells from liquid culture medium. Example embodiments described herein can promote a fast cell growth and a simple economical harvesting method that may be an improvement over existing methods. Example embodiments can include an algal growth system or mechanized harvesting system, which can remove concentrated algae in-situ from an attachment material and can minimize the amount of de-watering needed post-harvest. Example embodiments can optimize gas mass transfer due to the algae cells coming in direct contact with, for example, gaseous carbon dioxide when the algae are rotated through the open air. In an alternate embodiment, the algae can be rotated within an enclosed structure with natural or artificial grow lighting (e.g., LEDs). For example, the algae can be rotated within an enclosed greenhouse 40 (FIGS. 3 and 4) having an increased carbon dioxide concentration relative to the atmosphere, which may improve the growth rate of the algae. Example embodiments can utilize minimal growth medium, where the triangular or vertical design in example embodiments may reduce the total water needed for the growth and the chemical costs of growth medium. In one embodiment, such advantages may be accomplished by submerging only the lowest portion of a bioreactor, supporting material, algal growth system, or mechanized harvesting system into the medium.

Figure 2:
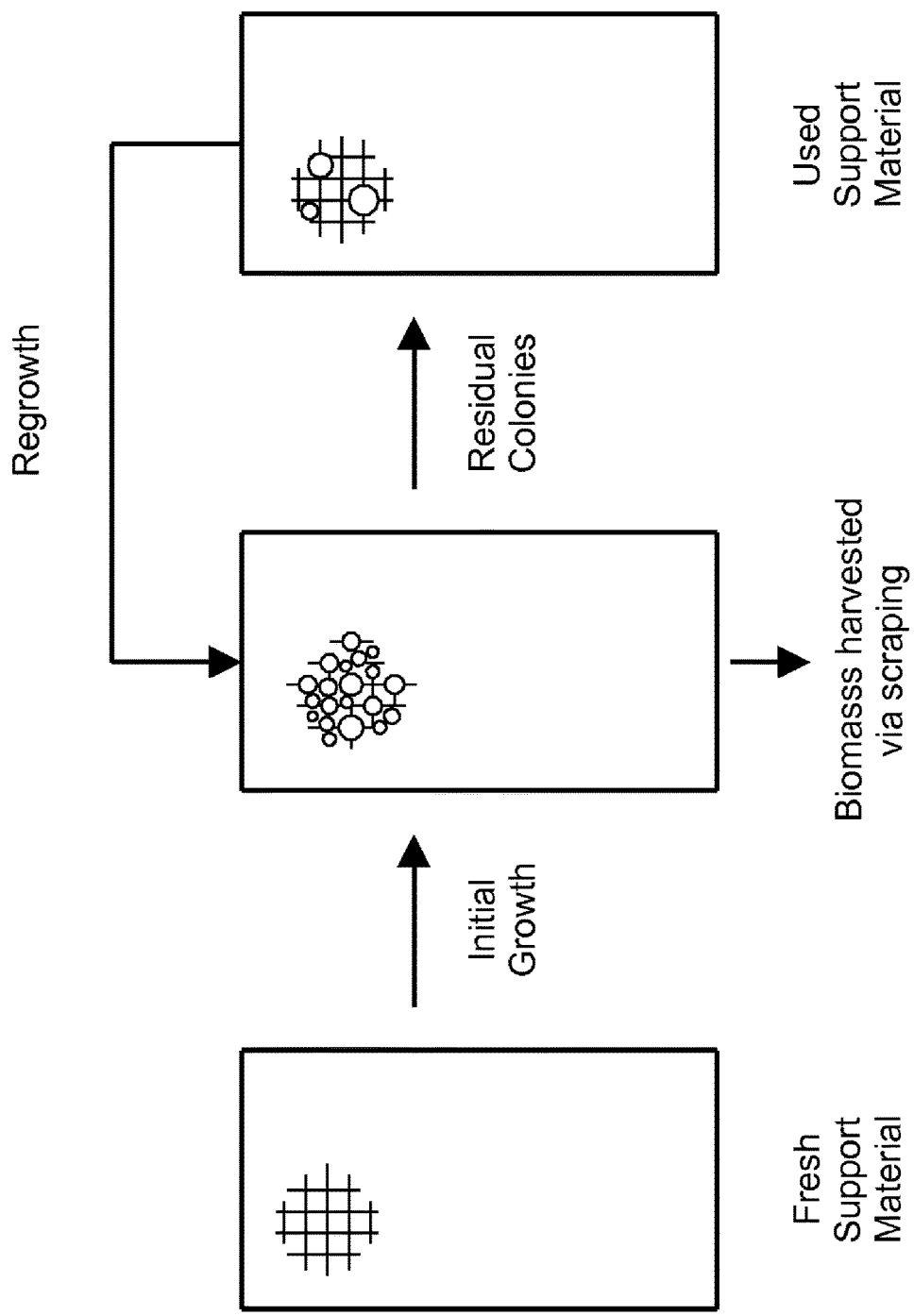
FIG. 2 depicts a top view of microalgae being grown on polystyrene foam.

Referring to FIG. 2, microalgae can be grown on the surface of polystyrene foam. FIG. 2 illustrates how algae can be harvested by scraping the surface of the foam. The mechanical separation through scraping of biomass from the attached materials can result in biomass with water content similar to centrifuged samples (e.g., 80-95% water content) and the residual biomass left on the surface can serve as an ideal inoculum for subsequent growth cycles.

Figure 3:
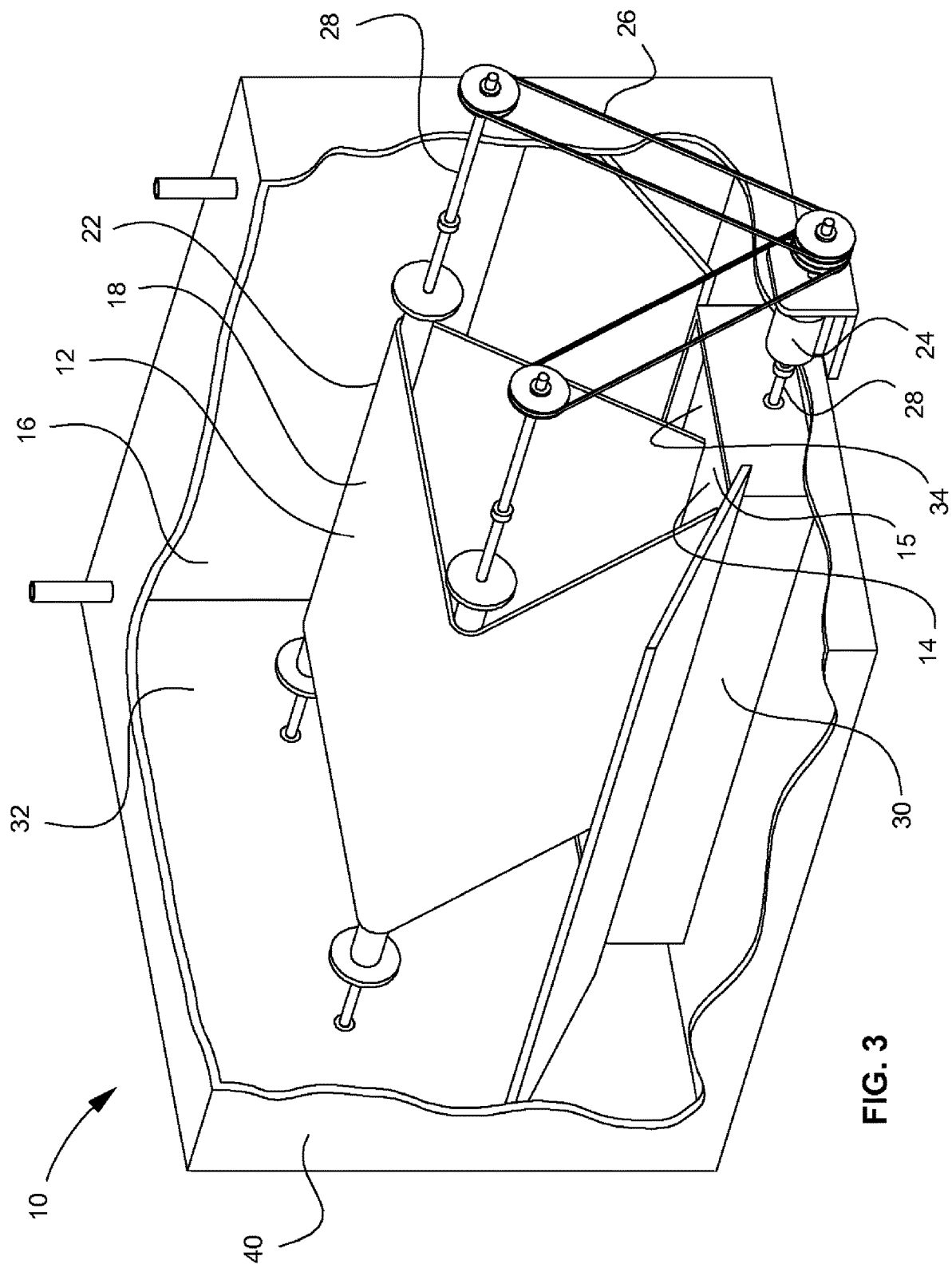
FIG. 3 depicts a partial cutaway perspective view of a revolving algal biofilm photobioreactor according to one embodiment.
Figure 4:
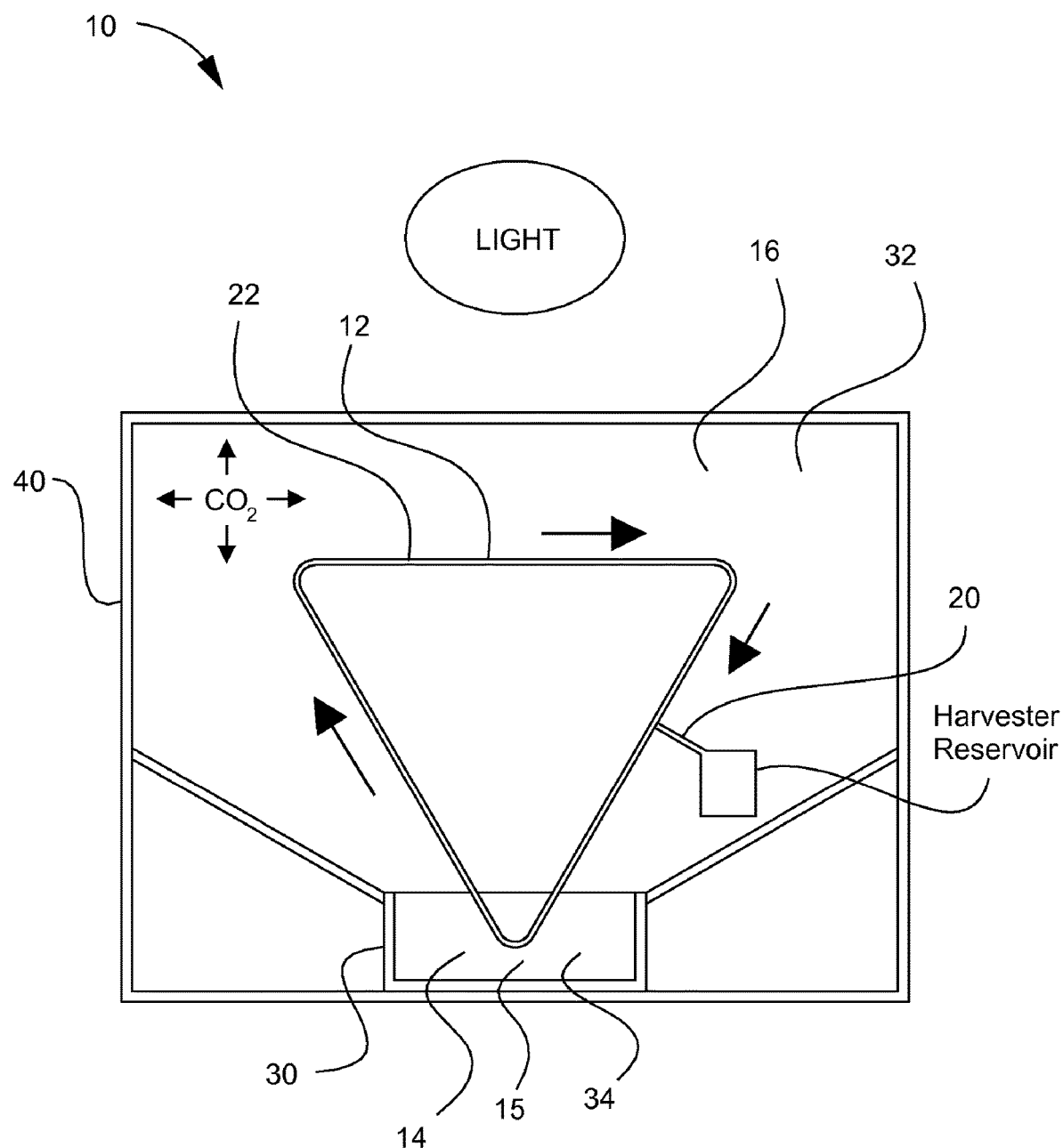
FIG. 4 depicts a schematic front view of the revolving algal biofilm photobioreactor illustrated in FIG. 3.
Figure 7:
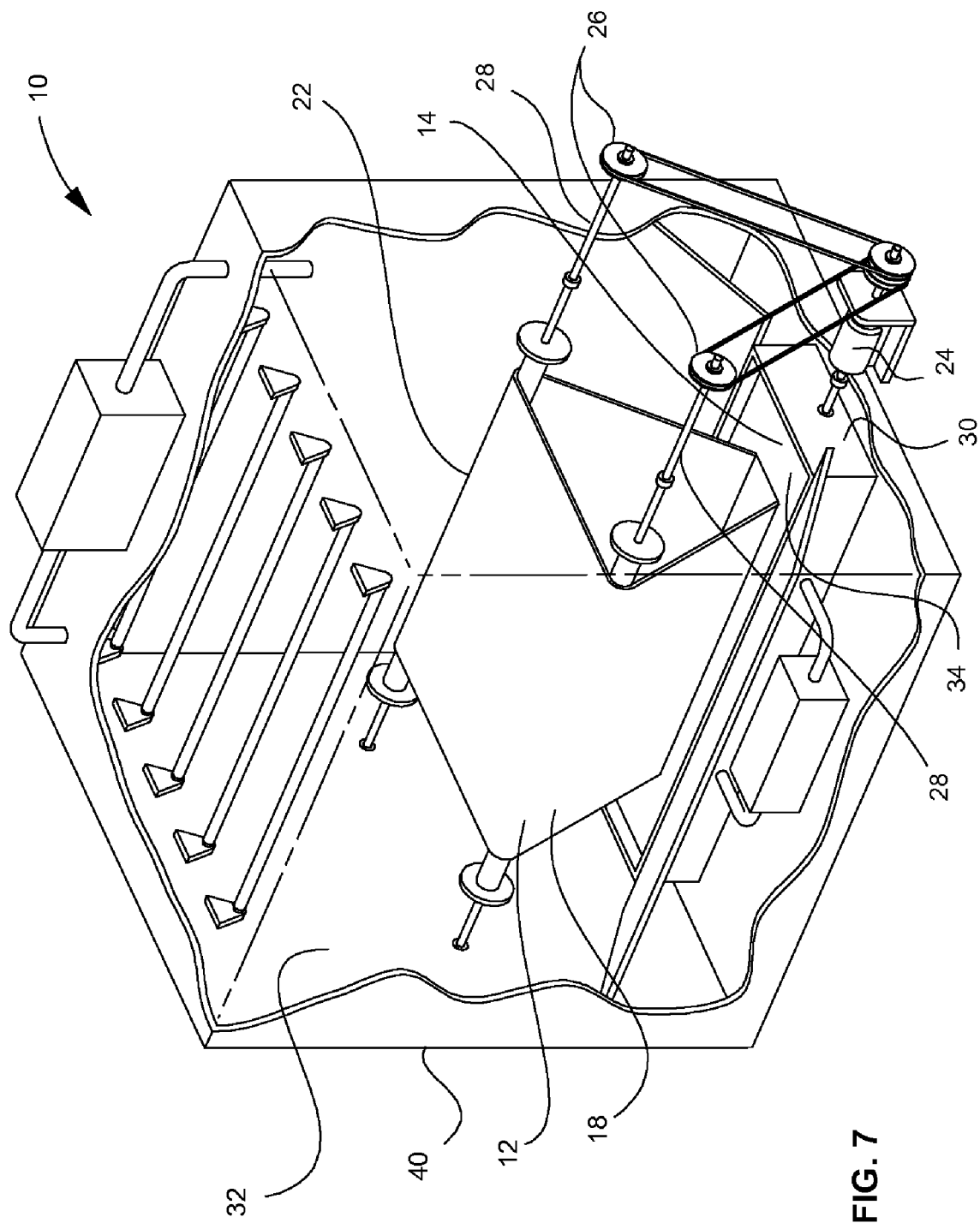
FIG. 7 depicts a partial cutaway perspective view of the revolving algal biofilm bioreactor illustrated in FIG. 3, shown with grow lights and a gas input.

Referring to FIGS. 3, 4, 7, and 8, an example embodiment of a revolving algal biofilm photobioreactor (RAB) 10, in which algal cells 18 can be attached to a solid surface of a supporting material 12, is disclosed. The photobioreactor 10 can keep the algal cells 18 fixed in one place and can bring nutrients to the cells, rather than suspend the algae in a culture medium. As shown in FIGS. 3 and 4, algal cells can be attached to the supporting material 12 that is rotating between a nutrient-rich liquid phase 15 and a $CO_2$-rich gaseous phase 16 for alternative absorption of nutrients and carbon dioxide. The algal biomass can be harvested by scraping the biomass from the attached surface with a harvesting scraper, such as squeegee 20 (FIG. 4), or other suitable device or system. In example embodiments, the naturally concentrated biofilm can be in-situ harvested during the culture process, rather than using an additional sedimentation or flocculation step for harvesting, for example. The culture can enhance the mass transfer by directly contacting algal cells with $CO_2$ molecules in gaseous phase, where traditional suspended culture systems may have to rely on the diffusion of $CO_2$ molecules from gaseous phase to the liquid phase, which may be limited by low gas-liquid mass transfer rate. Example embodiments may only need a small amount of water by submerging the bottom of the triangle-shaped algal growth system or mechanized harvesting system 22 in contacting liquid 14 while maximizing surface area for algae to attach. Example embodiments can be scaled up to an industrial scale because the system may have a simple structure and can be retrofit on existing raceway pond systems. Example embodiments can be used in fresh water systems and can be adapted to saltwater culture systems. For example, embodiments of this system can be placed in the open ocean instead of in a raceway pond reactor. In this example application, the ocean can naturally supply the algae with sufficient sunlight, nutrient, water, and $CO_2$, which in turn may decrease operational costs. Referring to FIG. 7, a gas input 43 and grow lights 42 having any suitable wavelength can be provided in the system.

Still referring to FIGS. 3, 4, 7, and 8, embodiments of the system can include a drive motor 24 and a gear system 26 that can rotate one or a plurality of drive shafts 28, where the one or a plurality of drive shafts 28 can correspondingly rotate the supporting material 12, such as a flexible sheet material. The supporting material 12 can be rotated into contact with the contacting liquid 14, which can allow the algal cells 18 to attach to the supporting material 12. The drive motor 24 can include a gear system 26 or pulley system that can drive the one or a plurality of drive shafts 28, where the one or a plurality of drive shafts 28 can rotate the supporting material 12 in and out of a contacting liquid 14, for example. Embodiments can also include a liquid reservoir 30, mister, water dripper, or any other suitable component or mechanism that can keep algae, which can be attached to the support material 12, moist. Embodiments can include any suitable scraping system, vacuum system or mechanism for harvesting the algal cells 18 from the supporting material 12. It will be appreciated that the system can include one or a plurality of rollers (not shown) that can be guide and support the supporting material 112 in addition to the one or a plurality of drive shafts 28.

In an example embodiment, a generally triangle-shaped mechanized harvesting system 22 can be provided. Such a configuration can be beneficial in maximizing the amount of sunlight or light that algal cells 18 are exposed to. However versions of the system can be designed, for example, in any configuration that includes a "sunlight capture" part 32 which can be exposed to air and sunlight, and a "nutrient capture" part 34 which can be submerged into a nutrient solution or contacting liquid 14. It will be appreciated that, in a first position, the supporting material 12 can have a portion that is in the "sunlight capture" part 32 and a portion that is in the "nutrient capture" part 34, where rotation of the supporting material 12 to a second position can result in different regions corresponding to the "sunlight capture" part 32 and "nutrient capture" part 34. Such movement of the supporting material 12 can, for example, beneficially transition algal cells 18 from a nutrient rich liquid to a region with sunlight and a carbon dioxide content higher than the outside atmosphere. As will be shown in more detail herein, a substantially vertical design is contemplated, which may be the simplest and most cost efficient design because such a system may minimize the amount of wasted space and may maximize the amount of algae produced in a small area by growing this system vertically. Alternative designs can include a straight vertical reactor, a reactor that is straight but slightly angled to provide more surface area for sunlight to hit, a cylindrical reactor, or a square shaped reactor.

Figure 8:
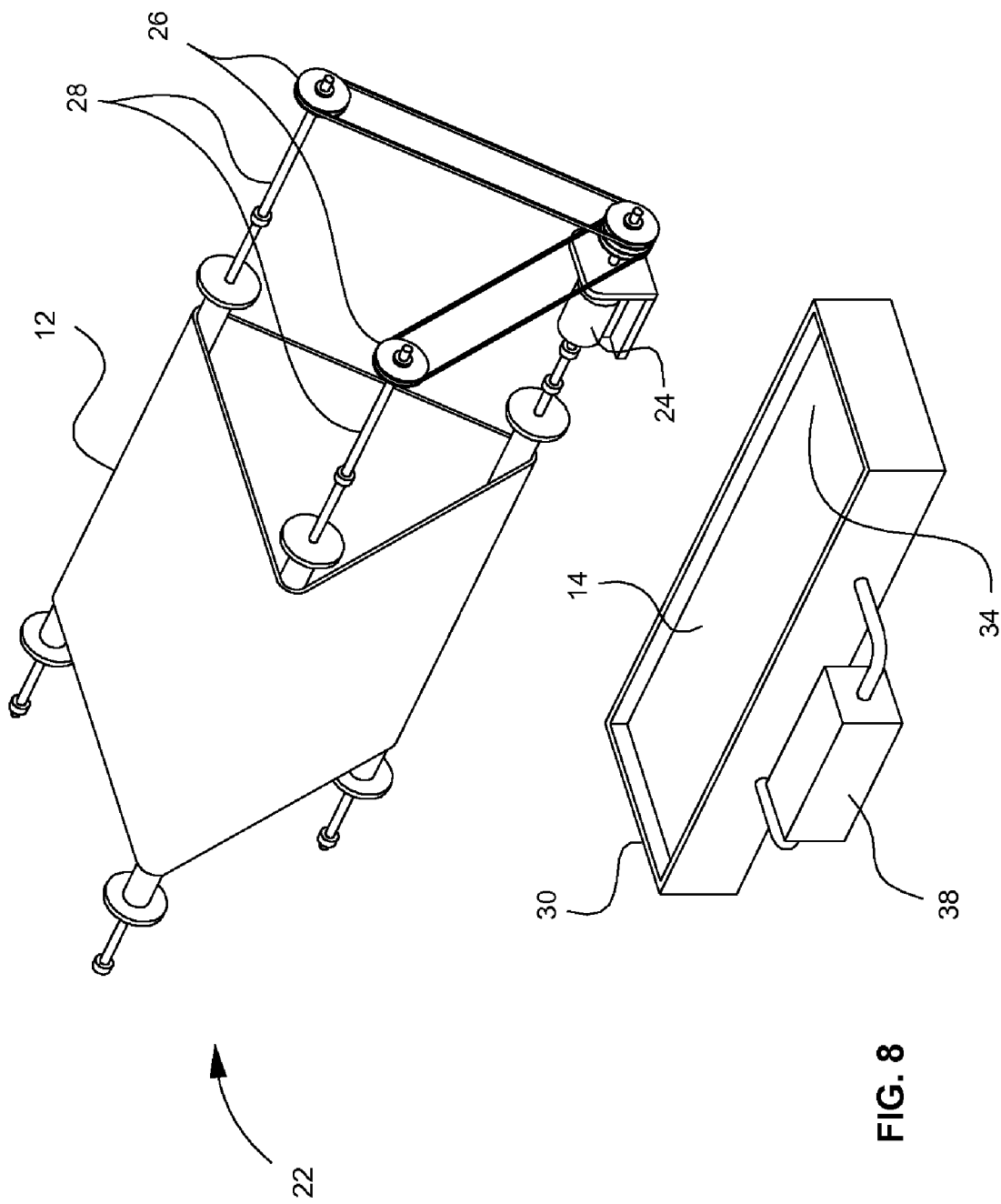
FIG. 8 depicts a partial exploded view of the revolving algal biofilm bioreactor shown in FIG. 3.

Referring to FIG. 8, the generally triangle-shaped algal growth and mechanized harvesting system 22 can include a supporting material 12 that is movable or removable relative to the liquid reservoir 30. The supporting material 12, and any associated components such as the one or a plurality of drive shafts 28 and gear system 26, can be movable or removable for cleaning, replacement, harvesting, adjustment, or the like. It will be appreciated that such movement can be manual or can be automated if desirable. In an example embodiment, the liquid reservoir 30 can contain a contacting liquid 14 having a first chemical or fluid makeup, where the supporting material 12 can be lifted or otherwise transitioned from the liquid reservoir 30 into a second liquid reservoir (not shown) having a second liquid (not shown) having a different chemical or fluid makeup from the contacting liquid 14. In this manner, the supporting material 12 retaining algal cells 18 can be dipped or transitioned into a variety of fluids or materials that may maximize algal growth or otherwise provide a benefit. Such a system can be repeated or adjusted as appropriate. In an alternate embodiment, the supporting material can be lifted or moved from the liquid reservoir 30 and transitioned to a harvesting station. In one embodiment, harvesting can take place while the supporting material 12 is positioned within the liquid reservoir 30.

Still referring to FIG. 8, the liquid reservoir 30 can include a pump 38 or any other suitable actuator or fluid control. The pump 38 can circulate the contacting liquid 14, which may improve the growth of algal cells 18 and the efficiency of the overall system. It will be appreciated that the pump 38 can be an electric pump, a wheel, a paddlewheel, or can have any other suitable configuration to create any desirable flow pattern. It will be appreciated that the pump 38 can heat, cool, or otherwise adjust the conditions associated with the contacting liquid 14. The pump 38 can also be configured for the delivery of supplemental nutrients, such as supplemental fluids delivered at pre-specified times, where such delivery can be manual or automated. It will be appreciated that the pump 38, and any other suitable components, can be associated with a computer, controller, or microcontroller that can be programmed to provide any suitable automated functionality.

Figure 5:
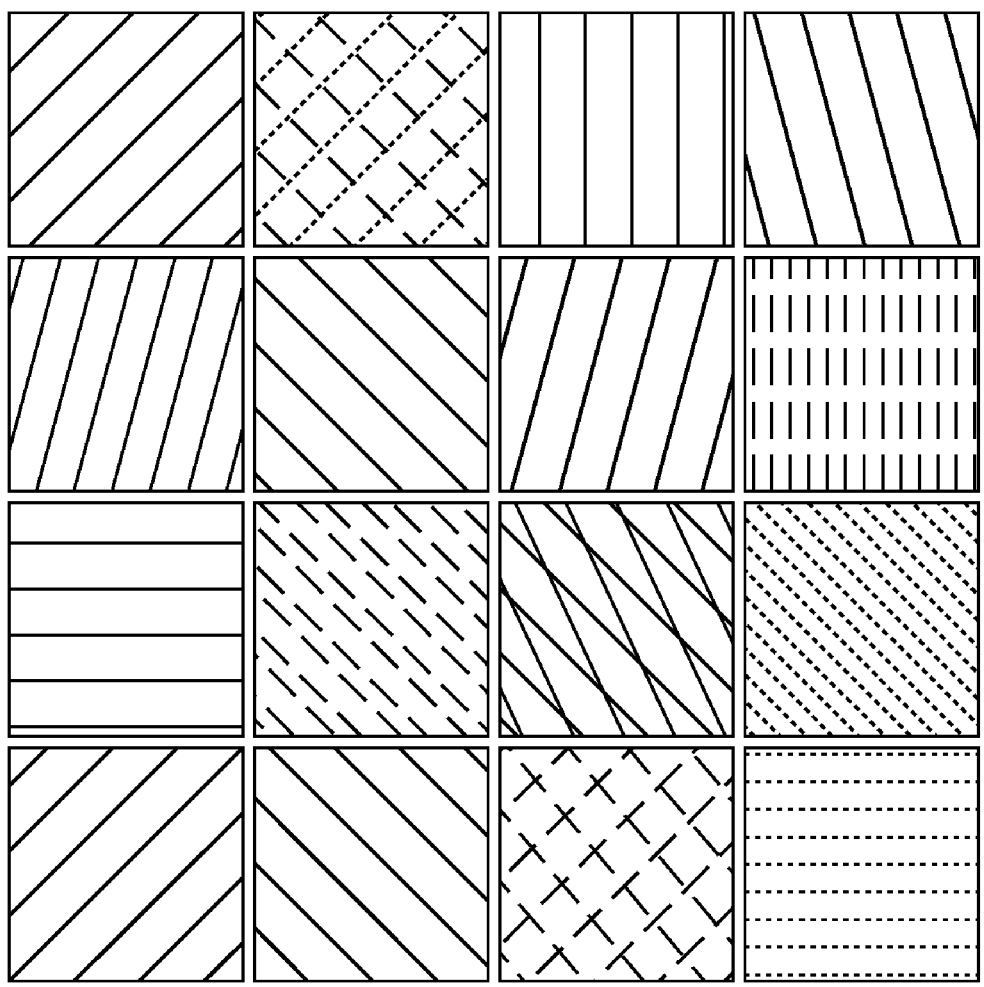
FIG. 5 depicts a top view of microalgae being grown on a variety of materials.

Referring to FIG. 5, any suitable supporting material 12, such as any suitable flexible fabric, can be used with the systems and methods described herein to grow any suitable material. The supporting material 12 may include one or more natural materials, one or more synthetic materials, or a combination thereof. For example, the microalga *Chlorella*, such as *Chlorella vulgaris* can be grown on materials such as, muslin cheesecloth, aramid fiberglass, porous PTFE coated fiberglass, chamois, vermiculite, microfiber, synthetic chamois, fiberglass, burlap, cotton duct, velvet, TYVEK, poly-lactic acid, abrased poly-lactic acid, vinyl laminated nylon, polyester, wool, acrylic, lanolin, woolen, cashmere, leather, silk, lyocell, hemp fabric, SPANDEX, polyurethane, olefin fiber, polylactide, LUREX®, carbon fiber, and combinations thereof. The supporting material or associated material can include rubbers such as, for example, buna-n rubber, butyl rubber, ECH rubber, EPDM rubber, gum rubber, polyethylene rubber, latex rubber, neoprene rubber, polyurethane, SANTOPRENE rubber, SBR rubber, silicone rubber, vinyl rubber, VITON fluoroelastomer, aflas, fluorosilicone, or combinations thereof. The supporting material or associated material can include plastics such as, for example, PETG, acrylic, cast acrylic, polycarbonate, LDPE, PLA, PVC, ABS, polystyrene, HDPE, polypropylene, UHMW, delrin, acetal resin, nylon, cast nylon, CPVC, REXOLITE polystyrene, NORYL PPO, polyester, PVDF, polysulfone, RADEL PPSU, ULTEM PEI, FEP, PPS, PEEK, PFA, TORLON PAI, TEFLON PTFE, polyimide, antistatic polycarbonate, antistatic cast acrylic, conductive ABS/PVC, antistatic acetal, atatic-dissipative UHMW, conductive UHMW, antistatic PTFE, glass-filled polycarbonate, strengthened acrylic, strengthened PVC, glass-filled nylon, glass-filled acetal, glass-filled UHMW, glass-filled PTFE, and combinations thereof. The supporting material and associated materials can include metals such as, for example, aluminum, steel, cast iron, tungsten carbide, tungsten alloy, stainless steel, nickel, titanium, copper, brass, bronze, lead, tin, zinc, casting alloys, or combinations thereof. Any suitable material for the supporting material and associated materials is contemplated including ceramic, felt, fiberglass, foam, foam rubber, foam plastic, glass, leathers, carbon fiber, wire cloth, cellulose, cellulosic or hemicellulosic materials from agricultural by-products, or the like, as well as combinations thereof.

Figure 18:
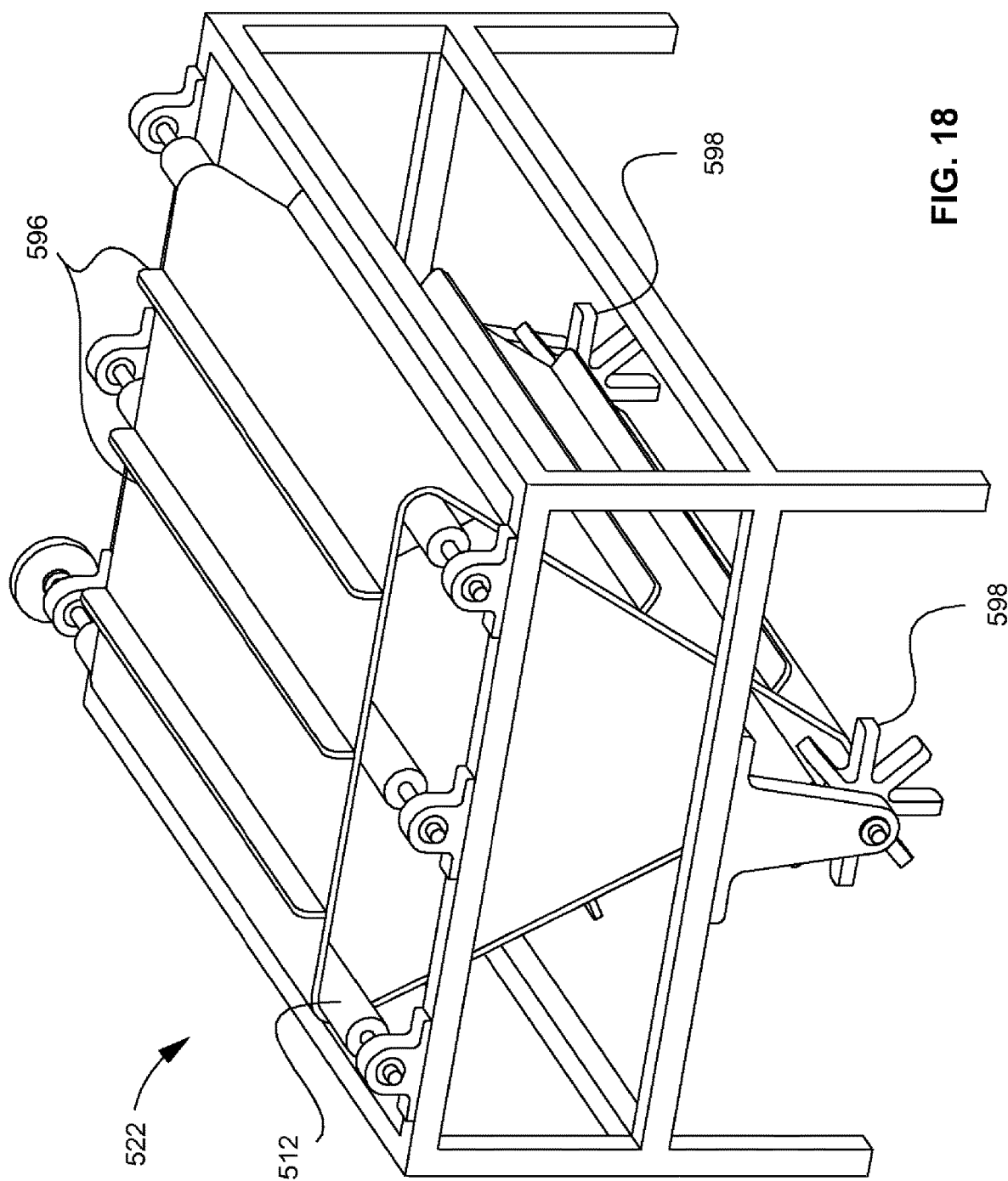
FIG. 18 depicts a perspective view of an algal growth system according to one embodiment.

The material associated with the supporting material 12 can have a high surface roughness, high hydrophobicity, and high positive surface charge in one embodiment. It will be appreciated that any suitable texture, surface treatment, hybrid material, or the like is contemplated. The supporting material, belt, sheet, or band can be altered, modified, or changed with heat, abrasion, applying another material, chemically treating, applying a charged molecule, applying a polar molecule, or combinations thereof. Referring to FIG. 18, in one embodiment of an algal growth system 522, the supporting material 512 can including one or a plurality of ribs 596, can be finned, or otherwise textured such that a pump is not needed to agitate an associated contacting liquid, where rotation of the textured supporting material can sufficiently agitate or otherwise create a desirable fluid dynamic. The algal growth system 522 can also include an integrated paddle 598 that can be positioned within a contacting liquid such that rotation of the supporting material 512 correspondingly can rotate the integrated paddle 598. In alternate embodiments, the supporting material can include flexible regions and rigid regions, can be a hinged belt, can have removable sections, or can otherwise be suitably configured. For example, in one embodiment, strips of material can be attached to a rotating belt with a hook and loop fastener, where such strips can be pulled off of the rotating belt during harvesting and replaced when harvesting is complete.

The supporting material 12 can be reinforced by attaching a high strength and slowly degradable second layer of material to a cell growth material. The photobioreactor 10 can be configured such that the high strength material comes in contact with components such as rollers, drive shafts, and the like. Such a configuration may help avoid the wearing off of the cell growth material during operation of the photobioreactor 10. Suitable materials can include materials that are not easily degraded by water and microbes such as plastic, rubber, TYVEK®, or other slowly degrading materials. Additionally, materials, adhesives, chemicals, or the like can be sprayed onto or otherwise provided on the supporting material 12 to facilitate algal attachment. It will be appreciated that any suitable number of layers of material is contemplated.

It will be appreciated that any suitable algal cells 18 (including cyanobacteria) as well as fungal strains, such as strains that can be used in aquaculture feed, animal feed, nutraceuticals, or biofuel production can be used. Such strains can include *Nannochloropsis* sp., which can be used for both biofuel production and aquacultural feed, *Scenedesmus* sp., a green microalga that can be used in wastewater treatment as well as for fuel production feedstock, Haematococcus sp, which can produce a high level of astaxanthin, *Botryococcus* sp. a green microalga with high oil content, *Spirulina* sp. a blue-green alga with high protein content, *Dunaliella* sp. a green microalga containing a large amount of carotenoids, the microalga *Chlorella*, such as *Chlorella vulgaris*, and/or other microalgae, such as one or more of a group of microalgae species producing a high level of long chain polyunsaturated fatty acids can include *Arthrospira, Porphyridium, Phaeodactylum, Nitzschia, Crypthecodinium* and *Schizochytrium*. Any suitable parameter, including gaseous phase $CO_2$ concentration, harvesting frequency, the rotation speed of the RAB reactor, the depth of the biofilm harvested, the ratio of submerged portion to the air-exposure portion of the RAB reactor, or the gap between the different modules of the RAB system can be optimized for any suitable species. It will be appreciated that the listed genus and species are described by way of example and additions and combinations are contemplated. It will also be appreciated that algal biofilm may include the algal cells as well as EPS, an associated fungus in the biofilm, associated microbes in the biofilm including bacteria (e.g., phosphorus accumulating bacteria, etc.), and combinations thereof.

Figure 6:
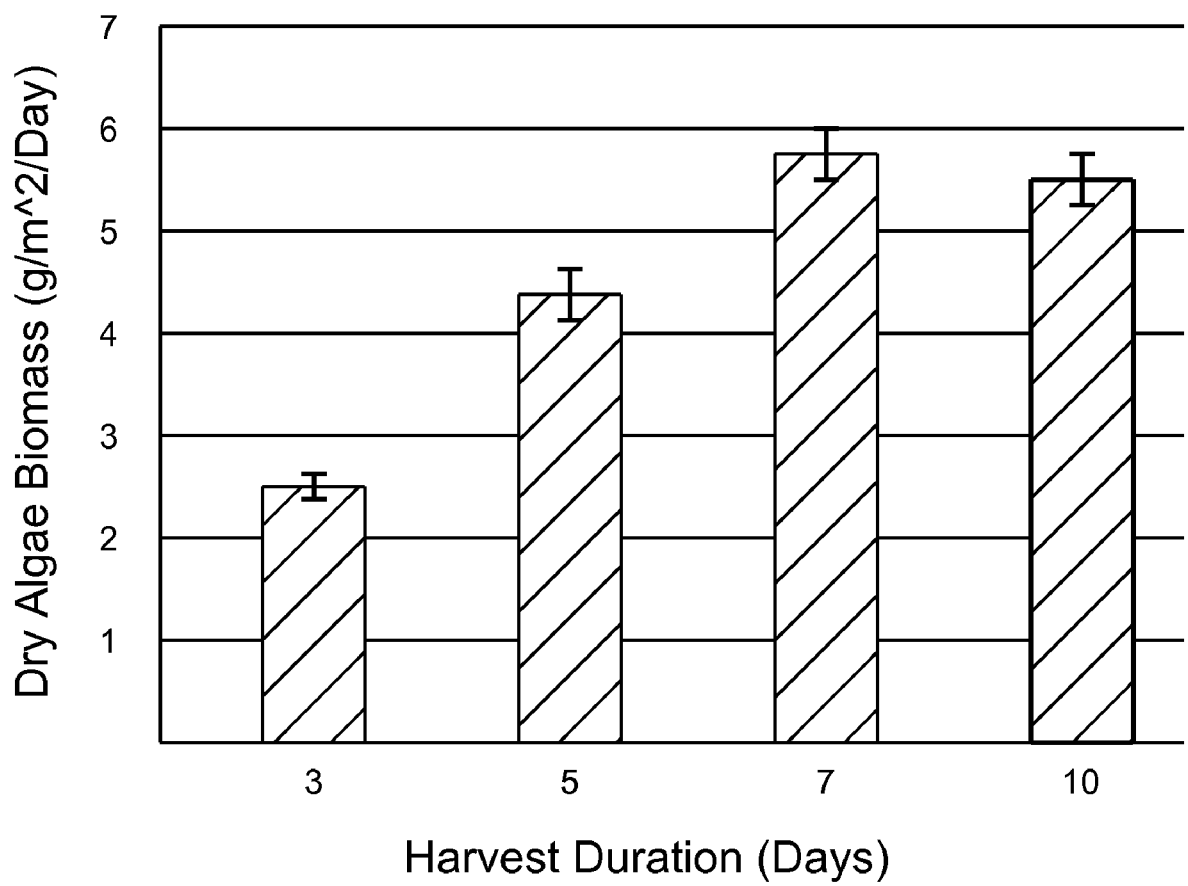
FIG. 6 depicts a bar chart of harvesting frequencies for an algal strain according to one embodiment.

Referring to FIG. 6, any harvesting schedule can be used in accordance with example embodiments described herein. The mechanism of harvesting biomass from the biofilm can be, for example, scraping, high pressure air, vacuum, or combinations thereof. Biomass productivity may vary by species and any suitable harvesting time is contemplated to maximize such productivity. For example, as shown in FIG. 6, of this specific species as a function of harvesting time by growing the algae on a RAB system then harvesting the cells at different durations. As shown in FIG. 6, for *Chlorella* the optimal harvest frequency may be every seven days. In example embodiments, managing other parameters such as $CO_2$ concentration and nutrient loading may also impact algal growth performance.

Figure 9:
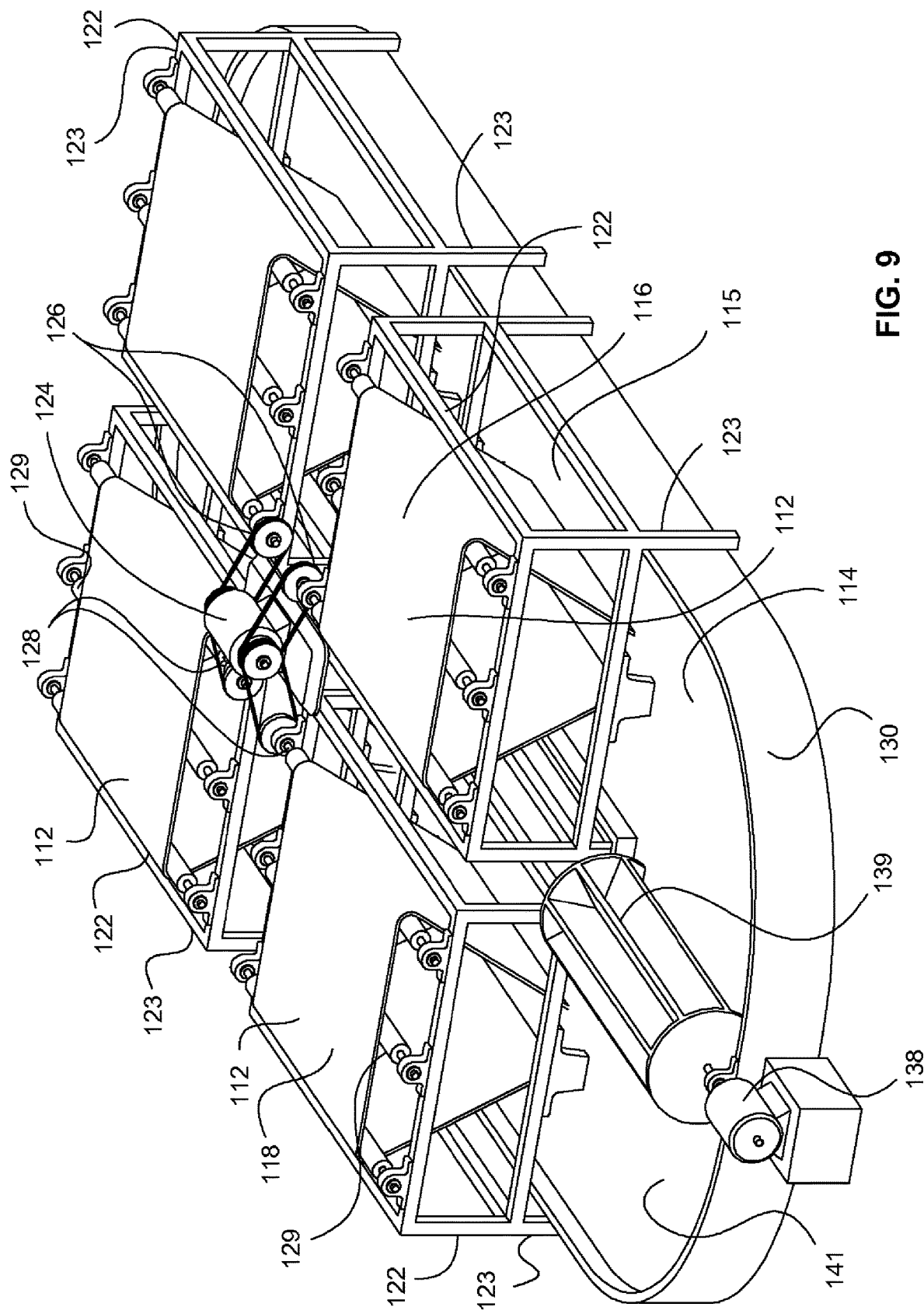
FIG. 9 depicts a perspective view of a revolving algal biofilm bioreactor having a plurality of associated algal growth systems and a raceway according to one embodiment.
Figure 10:
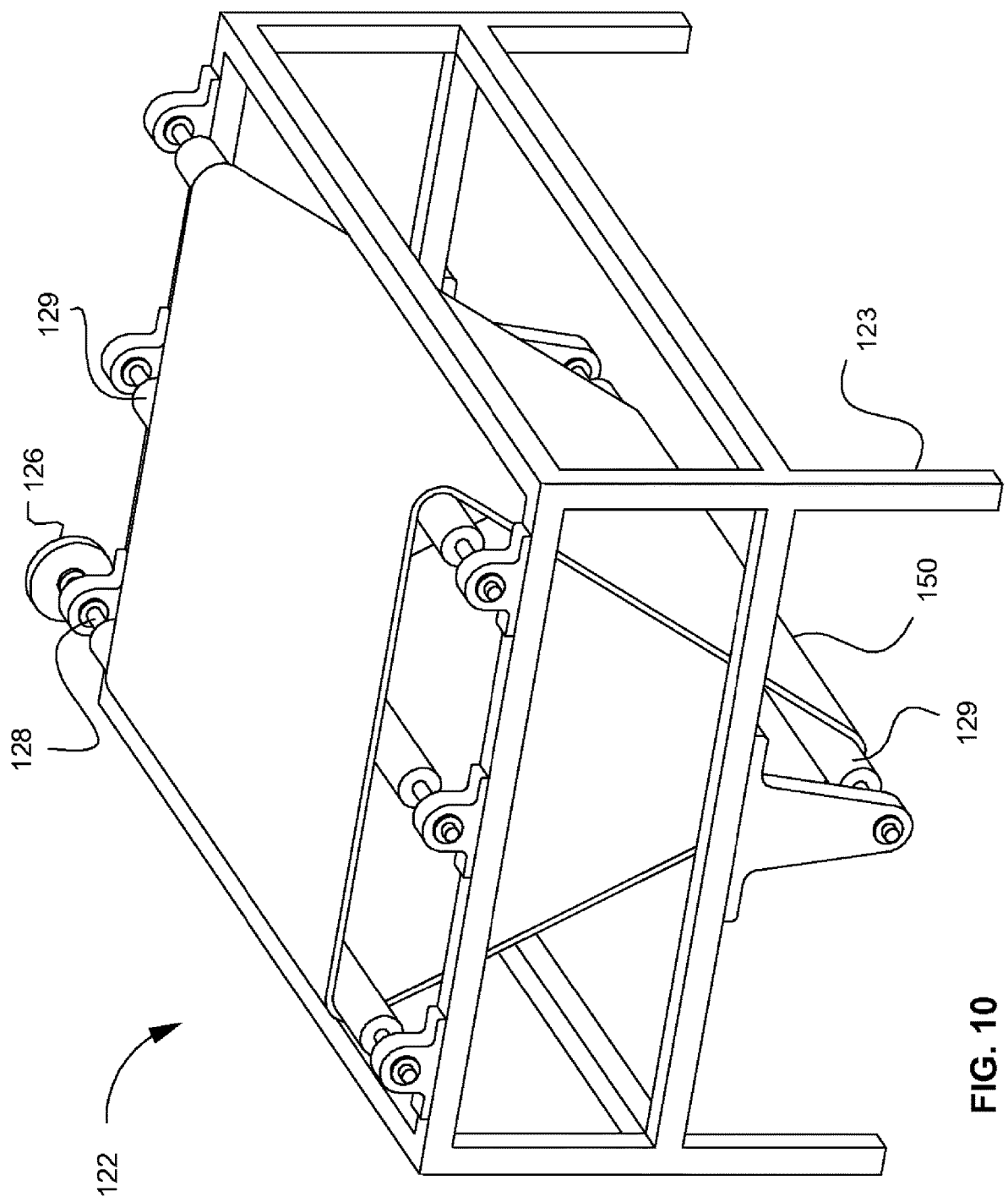
FIG. 10 depicts a perspective view of the algal growth system illustrated in FIG. 12.
Figure 11:
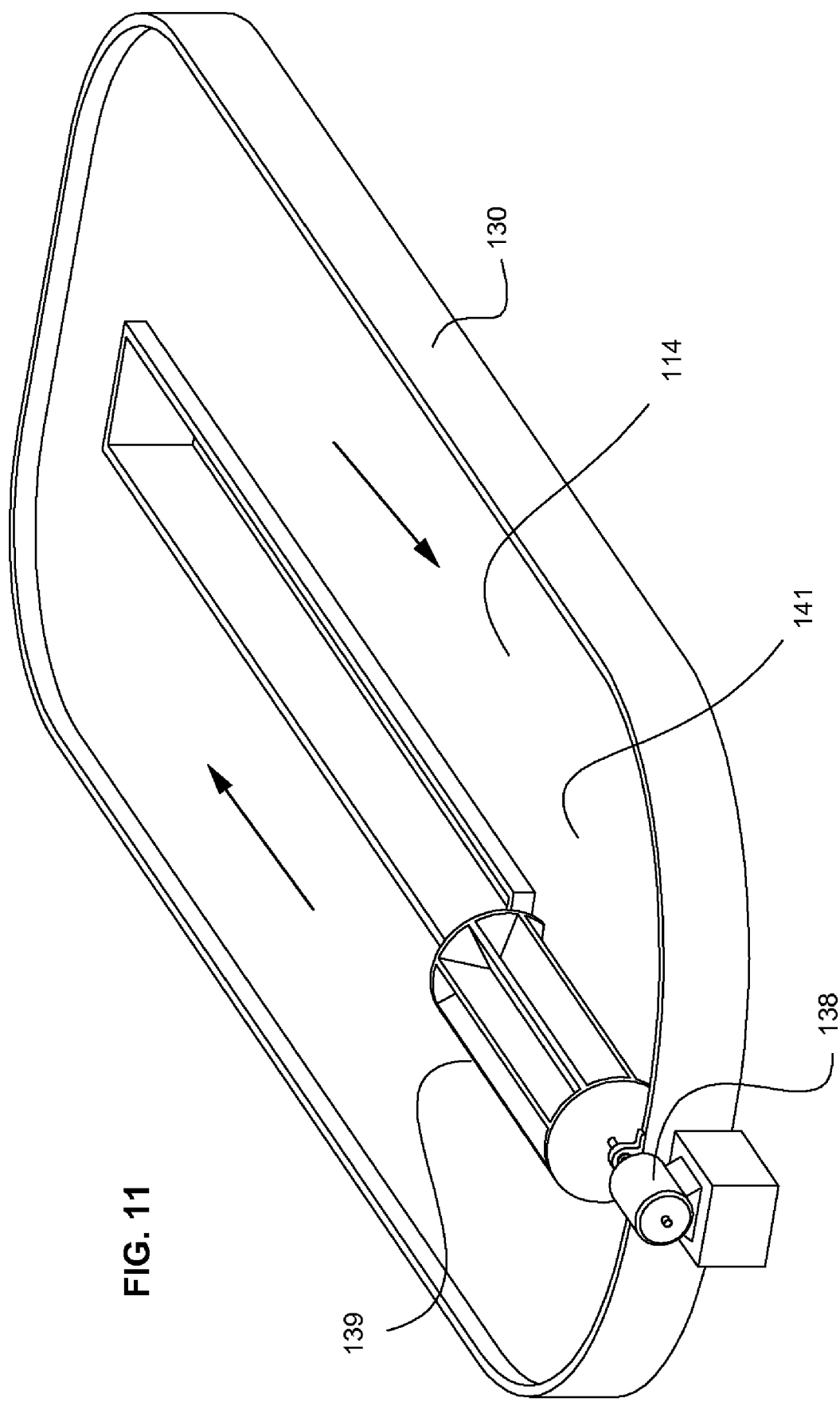
FIG. 11 depicts a perspective view of the raceway illustrated in FIG. 12.

Referring to FIGS. 9-11, shown is an alternate embodiment of a revolving algal biofilm photobioreactor (RABP) 100, in which algal cells 118 can be attached to a solid surface of a supporting material 112 that can be rotated between a nutrient-rich liquid phase 115 and a $CO_2$-rich gaseous phase 116 for alternative absorption of nutrients and carbon dioxide. The algal biomass can be harvested by scraping the biomass from the attached surface with a harvesting mechanism (not shown) such as a squeegee, vacuum, reaper, or the like. The photobioreactor 100 may require only a small amount of water for operation, relative to existing methods, where only the bottom 150 (FIG. 10) of an algal growth unit or mechanized harvesting unit 122 may be immersed in a contacting liquid 114. The photobioreactor 100 can include one or a plurality of mechanized harvesting units 122, having frames 123, that can be positioned in a raceway 130 containing contacting fluid 114. Example embodiments can include a large number of mechanized harvesting units such that the photobioreactor can be scaled up to an industrial scale. For example, a single raceway could have 20, 50, 100, or more mechanized harvesting units. In an example embodiment, the one or a plurality of mechanized harvesting units 122 can be retrofitted onto existing raceway pond systems. Example embodiments can be used in fresh water systems and can be also be adapted to saltwater culture systems. In one example, the ocean can naturally supply the algal cells with sufficient sunlight, nutrient, water, and $CO_2$, which in turn may decrease operational costs associated with operation of a photobioreactor. Embodiments of the mechanized harvesting units can be placed, for example, in any suitable fluid retaining location or device. Further, embodiments of the photobioreactor 100 can be positioned in a fluid reservoir that is either natural (e.g., rivers, lakes, etc.) or manmade (e.g., concrete tanks, etc.).

Embodiments of the photobioreactor 100 can include a drive motor 124 and a gear system 126 that can rotate one or a plurality of drive shafts 128, where the one or a plurality of drive shafts 128 can correspondingly rotate the supporting material 112, such as a flexible sheet material for growing algal cells 118. The photobioreactor 100 can include one or a plurality of rollers 129 that can support and guide the supporting material 112. The supporting material 112 can be rotated into contact with the contacting liquid 114, which can allow the algal cells 118 to attach to the supporting material 112. The drive motor 124 can include a gear system 126 or pulley system that can drive the one or a plurality of drive shafts 128, where the one or a plurality of drive shafts 128 can rotate the supporting material 112 into and out of the contacting liquid 114. Embodiments can also include a raceway 130, mister, water dripper, or any other suitable component or mechanism that can keep algae, which can be attached to the support material 112, moist. Embodiments can include any suitable scraping system, vacuum system or mechanism for harvesting the algal cells 118 from the supporting material 112. It will be appreciated that the drive motor 124 can be associated with a plurality of mechanized harvesting units 122 or, in an alternate embodiment, each mechanized harvesting unit can be associated with an independent motor, gear, and/or drive shaft system. It may be efficient to operate one or more of the mechanized harvesting units on the same schedule, but it may also be advantageous to operate some or all of the mechanized harvesting units on different schedules. For example, in one embodiment, a mechanized harvesting unit exposed to natural light can be associated with a light sensor (not shown) and controller (not shown) such that the rotation speed of the supporting material is optimized relative to the available light. In such an example, mechanized harvesting units in the same facility may have different, or slightly different environmental conditions, where operating each mechanized harvesting unit independently may substantially optimize the overall system.

The mechanized harvesting unit 122 can have a generally triangle-shaped configuration supported by the frame 123. It will be appreciated that the frame 123 can be constructed from any suitable material, such as metal, and can have any suitable configuration. The frame 123 can be substantially level relative to a flat surface, can be stepped, or otherwise shaped to accommodate an incline or an uneven surface. The frame 123 can include telescoping components (not shown), such as telescoping legs, which may allow the frame to be used effectively as a retrofit in existing raceways, for example. The frame 123 can be stackable (not shown) or can be coupled in a side-by-side fashion with other frames in an interlocking manner such that a plurality of mechanized harvesting systems can be connected to form a photobioreactor. Such a modular system may allow for a few mechanized harvesting system designs to be used in a wide variety of locations and situations.

One or a plurality of mechanized harvesting units 122 can be associated with the raceway 130 in any suitable manner or configuration. For example, each mechanized harvesting unit 122 can be integral with or permanently affixed to the raceway 130. In an alternate embodiment, each mechanized harvesting unit 122 can be selectively removable or adjustable relative to the raceway 130, where the mechanized harvesting unit 122 can be removed for cleaning, harvesting, replacement, upgrade, or the like.

Referring to FIG. 11, the raceway 130 can have any suitable shape or configuration. In one example, the raceway 130 can include a motor 138 that can be configured to drive a paddlewheel 139. The paddlewheel 139 can be configured to create a current or flow within the raceway 130 that may facilitate the growth of algal cells 118. It will be appreciated that the raceway, motor, and paddlewheel are shown by way of example only, where any suitable mechanism to provide a desirable flow or current in a suitable reservoir is contemplated. The raceway 130 can be open or otherwise exposed to light such that algae can easily grow within the raceway 130. The raceway 130 can have a region 141 that can be exposed to light and may not contain a mechanized harvesting unit, where the region 141 can be used to cultivate or grow a supply of algal cells 118 within the raceway 130. Providing such a region 141, where the region 141 can have any suitable shape or configuration, may make the system self-sustaining and may reduce the likelihood that the system needs to be seeded or re-seeded with algal cells.

Figure 12:
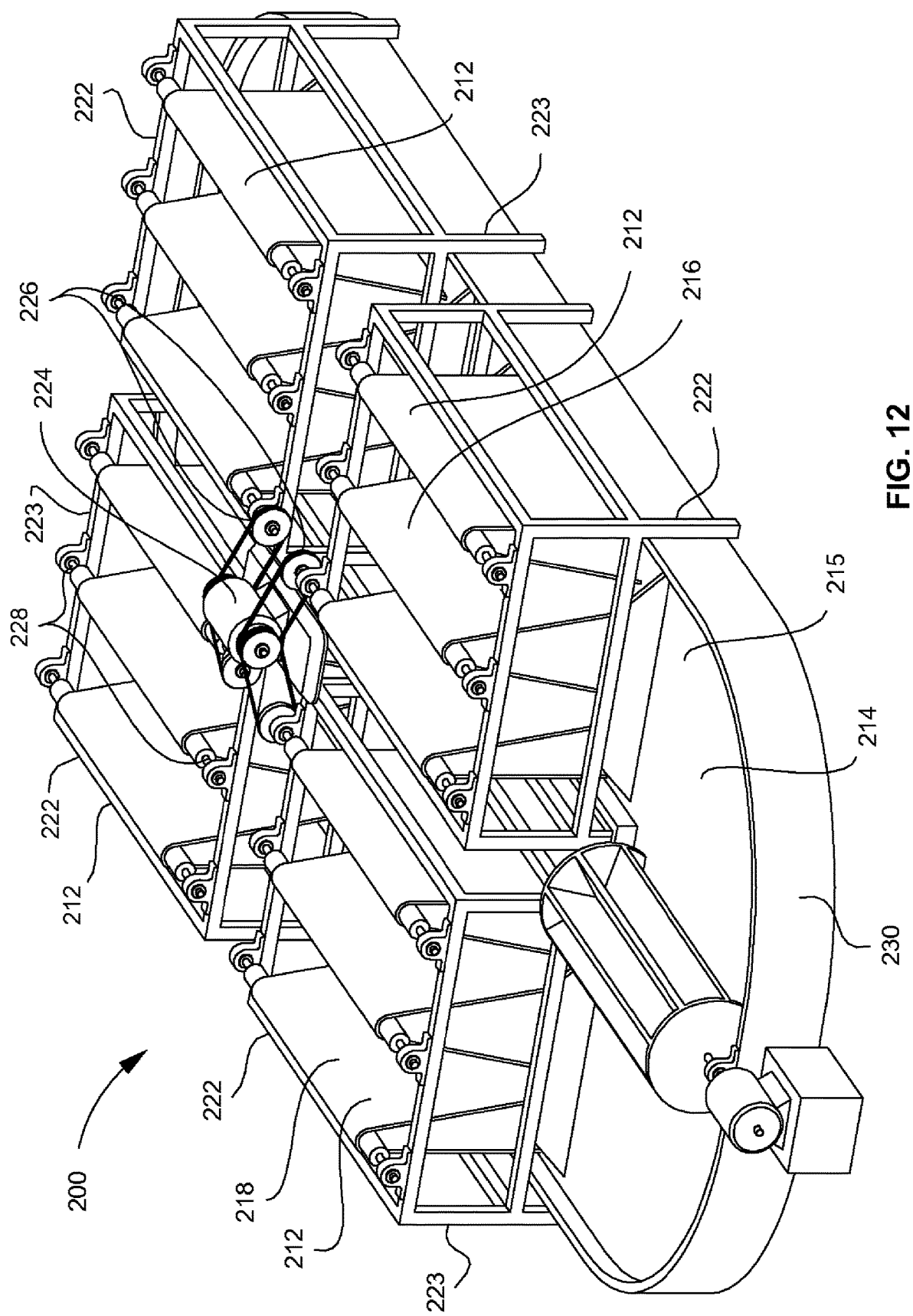
FIG. 12 depicts a perspective view of a revolving algal biofilm bioreactor having a plurality of associated algal growth systems and a raceway according to an alternate embodiment.
Figure 13:
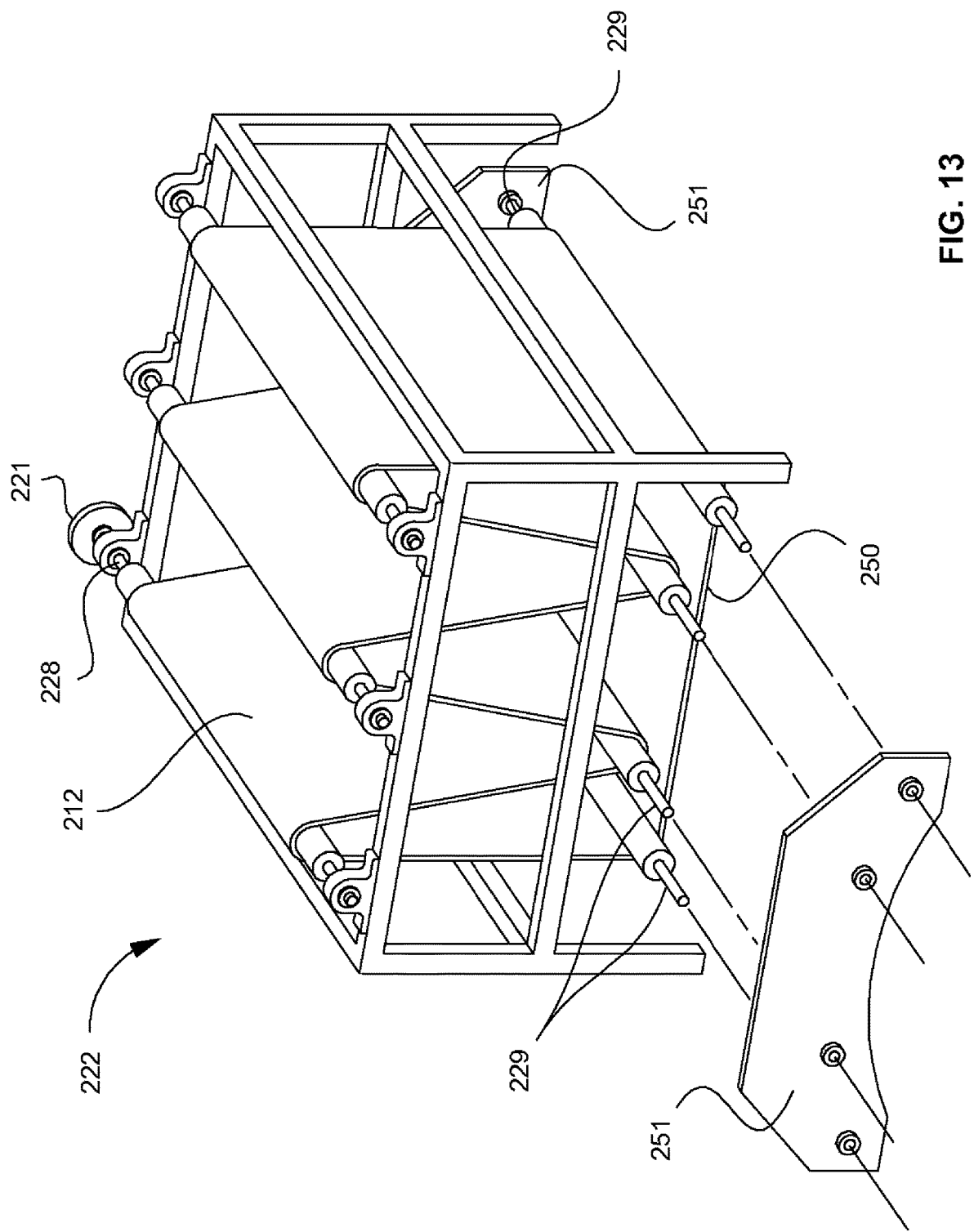
FIG. 13 depicts a perspective view of the algal growth system illustrated in FIG. 12.

Referring to FIGS. 12 and 13, shown is an alternate embodiment of a revolving algal biofilm photobioreactor (RAB) 200, in which algal cells 218 can be attached to a solid surface of a supporting material 212 that can be rotated between a nutrient-rich liquid phase 215 and a $CO_2$-rich gaseous phase 216 for alternative absorption of nutrients and carbon dioxide. The algal biomass can be harvested by scraping the biomass from the attached surface with a harvesting mechanism (not shown) such as a squeegee, vacuum, reaper, or the like. The photobioreactor 200 may require only a small amount of water for operation, relative to existing methods, where only the bottom 250 (FIG. 13) of an algal growth unit or mechanized harvesting unit 222 may be immersed in a contacting liquid 214. The photobioreactor 200 can include one or a plurality of mechanized harvesting units 222, having frames 223, which can be positioned in a raceway 230 containing contacting fluid 214. Example embodiments can include a large number of mechanized harvesting units such that the photobioreactor can be scaled up to an industrial scale. For example, a single raceway could have 20, 50, 100, or more mechanized harvesting units. In an example embodiment, the one or a plurality of mechanized harvesting units 222 can be retrofitted onto existing raceway pond systems. Embodiments of the mechanized harvesting units can be placed, for example, in any suitable fluid retaining location or device.

Embodiments of the photobioreactor 200 can include a drive motor 224 and a gear system 226 that can rotate one or a plurality of drive shafts 228, where the one or a plurality of drive shafts 228 can correspondingly rotate the supporting material 212, such as a flexible sheet material for growing algal cells 218. The photobioreactor 200 can include one or a plurality of rollers 229 that can support and guide the supporting material 112. The supporting material 212 can be rotated into contact with the contacting liquid 214, which can allow the algal cells 218 to attach to the supporting material 212. The drive motor 224 can include a gear system 226 or pulley system that can drive the one or a plurality of drive shafts 228, where the one or a plurality of drive shafts 228 can rotate the supporting material 212 into and out of the contacting liquid 214. Embodiments can also include a raceway 230, mister, water dripper, or any other suitable component or mechanism that can keep algae, which can be attached to the support material 212, moist. Embodiments can include any suitable scraping system, vacuum system or mechanism for harvesting the algal cells 218 from the supporting material 212. It will be appreciated that the drive motor 224 can be associated with a plurality of mechanized harvesting units 222 or, in an alternate embodiment, each mechanized harvesting unit can be associated with an independent motor, gear, and/or drive shaft system. It may be efficient to operate one or more of the mechanized harvesting units on the same schedule, but it may also be advantageous to operate some or all of the mechanized harvesting units on different schedules. For example, in one embodiment, a mechanized harvesting unit exposed to natural light can be associated with a light sensor (not shown) and controller (not shown) such that the rotation speed of the supporting material is optimized relative to the available light. In such an example, mechanized harvesting units in the same facility may have different, or slightly different environmental conditions, where operating each mechanized harvesting unit independently may substantially optimize the overall system.

The mechanized harvesting unit 222 can have a generally wave-shaped configuration supported by the frame 223. It will be appreciated that the frame 223 can be constructed from any suitable material, such as metal, and can have any suitable configuration in accordance with embodiments described herein. The supporting material 212 of the mechanized harvesting unit can have a substantially wave-shaped configuration as best illustrated in FIG. 13. The supporting material 212 can be a contiguous band of material and can be wound about the one or a plurality of drive shafts 228 or rollers 229 such that any suitable configuration is created. It is contemplated that the supporting material can be a long, contiguous band of material having multiple peaks and valley, as illustrated in FIG. 12. As illustrated, a portion of the supporting material 212 can also pass along the bottom 250 of the mechanized harvesting unit 222. It will be appreciated that a single long band and a plurality of bands having any suitable relationship or configuration are contemplated. In an example embodiment, the one or a plurality of drive shafts 228 or rollers 229 can be adjusted such that different configuration can be created using the same frame 223. Such an interchangeable system may be beneficial in that certain configurations may be beneficial to particular species of algal cells. An interchangeable system may also allow for different environmental conditions, uses, or use on a wide range of scales. Any other suitable component, such as a plate 251 can be provided to secure components, such as the rollers 229, in a desired configuration.

Figure 14:
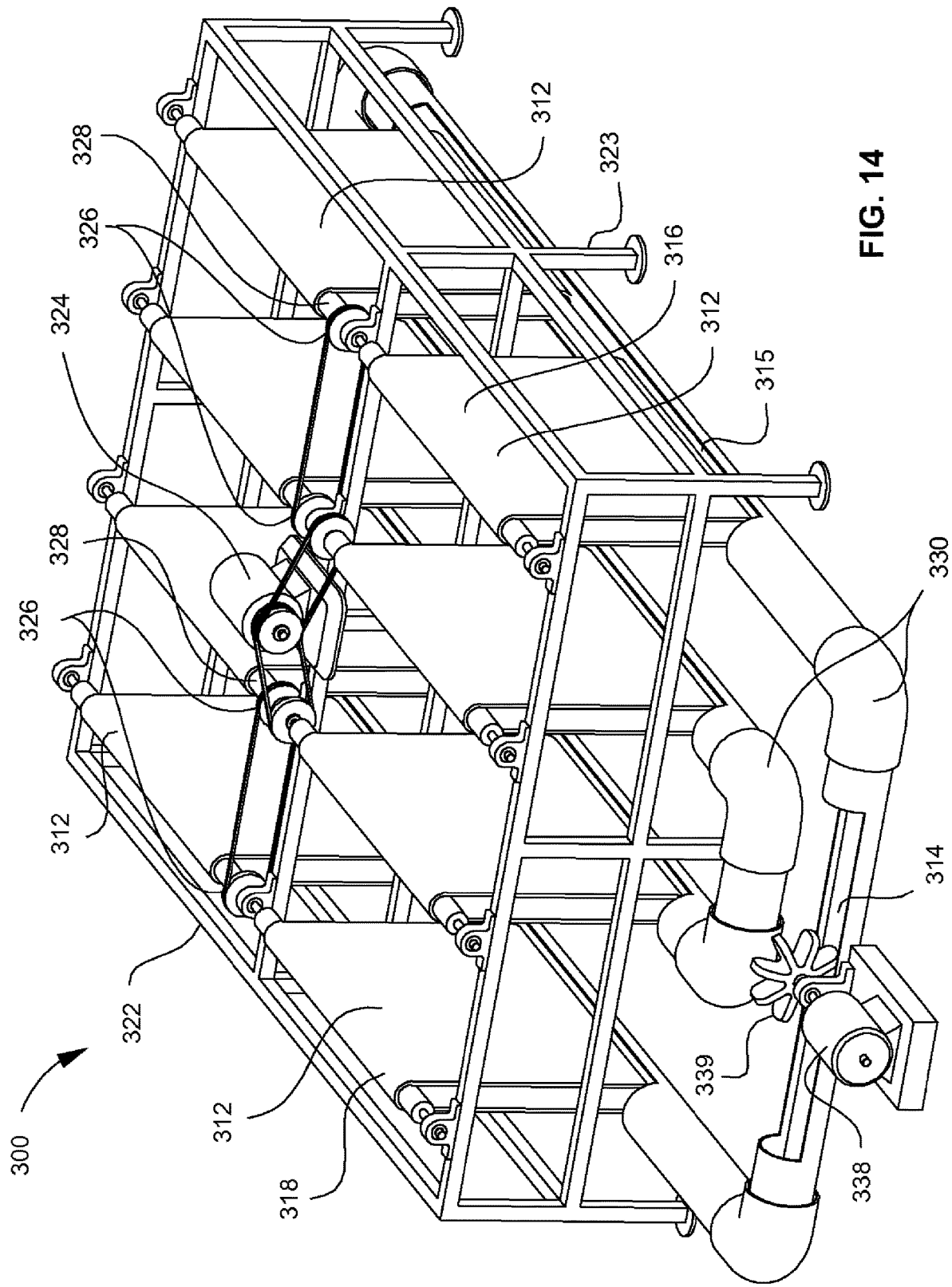
FIG. 14 depicts a perspective view of a revolving algal biofilm bioreactor having an associated algal growth system and a trough system according to one embodiment.
Figure 15:
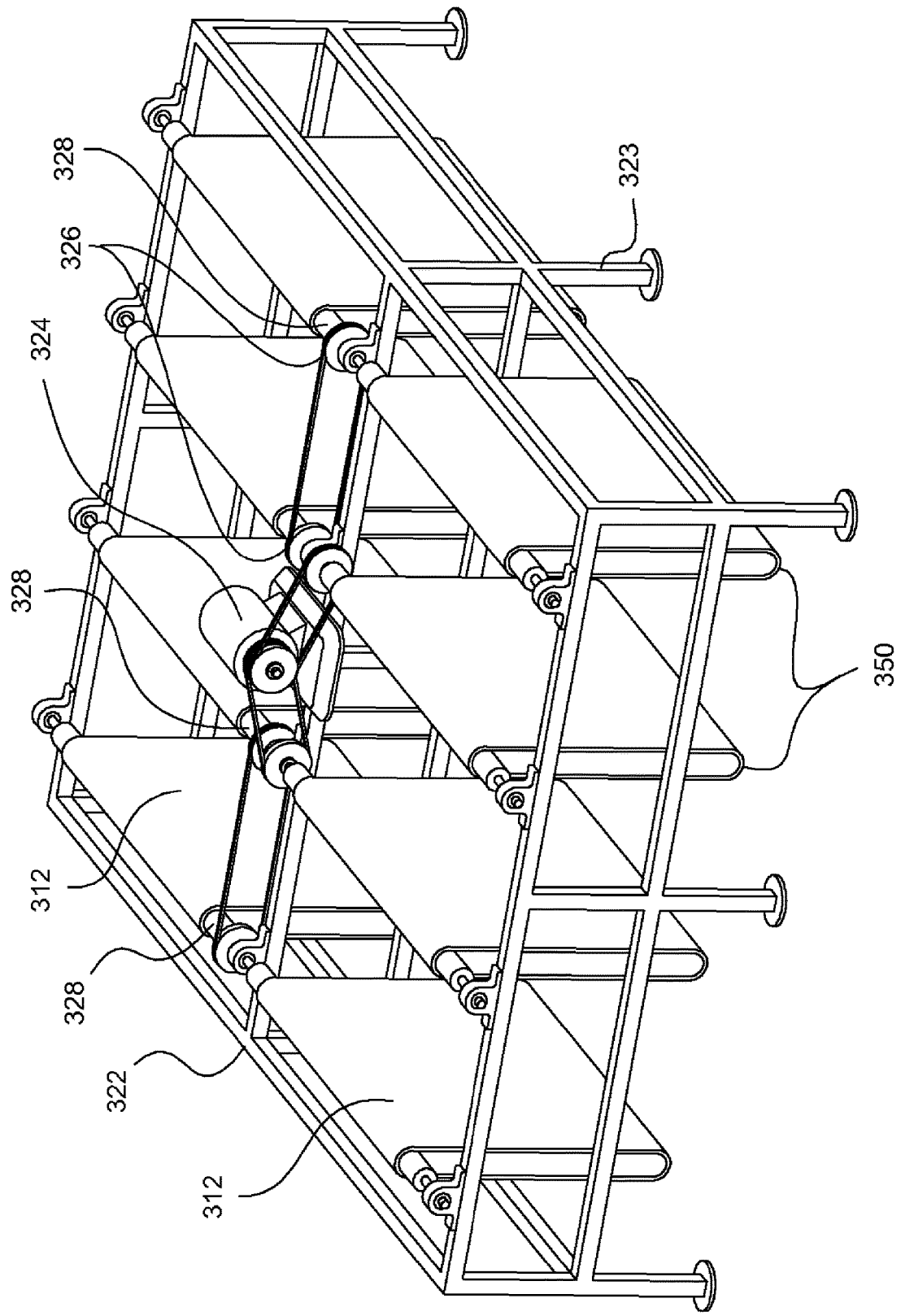
FIG. 15 depicts a perspective view of the algal growth system illustrated in FIG. 14.
Figure 16:
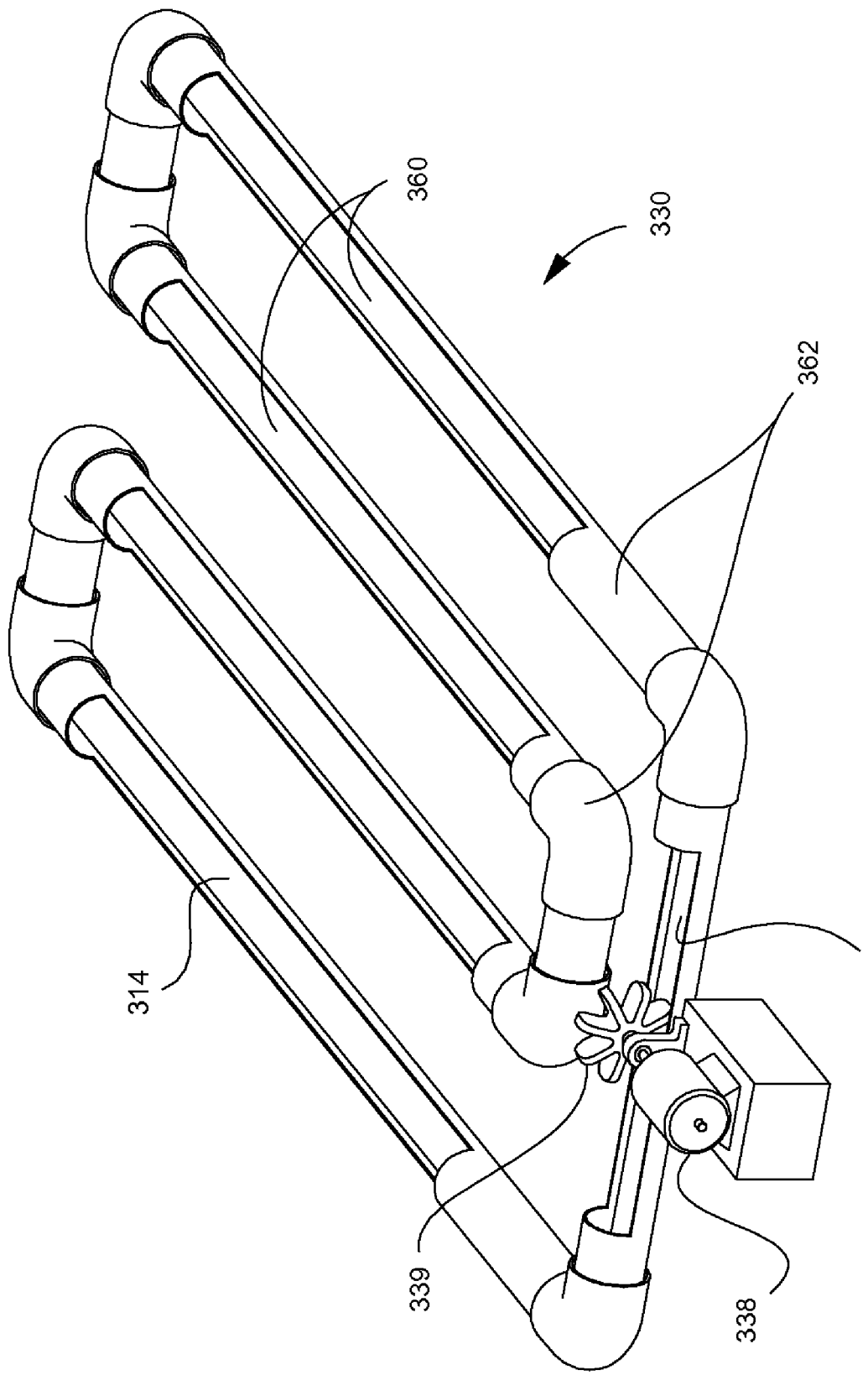
FIG. 16 depicts a perspective view of the trough system illustrated in FIG. 14.

Referring to FIGS. 14-16, shown is an alternate embodiment of a revolving algal biofilm photobioreactor (RAB) 300, in which algal cells 318 can be attached to a solid surface of one or a plurality of supporting materials 312 that can be rotated between a nutrient-rich liquid phase 315 and a $CO_2$-rich gaseous phase 316 for alternative absorption of nutrients and carbon dioxide. The algal biomass can be harvested by scraping the biomass from the attached surface with a harvesting mechanism (not shown) such as a scraper (e.g., a squeegee), vacuum, reaper, or the like. The photobioreactor 300 may require only a small amount of water for operation, relative to existing methods, where only the bottom 350 (FIG. 15) of an algal growth unit or mechanized harvesting unit 322 may be immersed in a contacting liquid 314. The photobioreactor 300 can include a frame 323, which can be positioned in a trough system 330 containing contacting fluid 314. Example embodiments can include a large number of mechanized harvesting units such that the photobioreactor can be scaled up to an industrial scale. For example, a single trough system could have 20, 50, 100, or more mechanized harvesting units or independent supporting material units. In an example embodiment, the one or a plurality of mechanized harvesting units 322 can be retrofitted onto existing raceway pond systems. Embodiments of the mechanized harvesting units can be placed, for example, in any suitable fluid retaining location or device.

It will be appreciated that the trough system 330 is show by way of example only, where any suitable tubing, configuration, or construction is contemplated. The trough system 330 can have a serpentine configuration such that the trough system 330 forms a substantially closed circuit for fluid flow. The trough system 330 can have any suitable shape, where the trough system 330 can have interchangeable parts such that different configurations can be created by a user. The trough system can include any suitable number of apertures 360 and closed sections 362, where apertures 360 can be configured to accept each of the one or a plurality of supporting materials 312. In one embodiment, the apertures 360 can be associated with a closure when not in use. Alternatively, apertures 360 can be used in sunlight or well lighted areas to help facilitate algal growth in the contacting liquid 314. The trough system 330 can be associated with a motor 338 and paddlewheel 339 that can be configured to create a fluid dynamic or current flow in the trough system 330. In one embodiment, one or a plurality of paddlewheels 339, or other actuators, can be positioned in the apertures 360.

Embodiments of the photobioreactor 300 can include a drive motor 324 and a gear system 326 that can rotate one or a plurality of drive shafts 328, where the one or a plurality of drive shafts 328 can correspondingly rotate the one or a plurality of supporting materials 312, such as a flexible sheet material for growing algal cells 318. The photobioreactor 300 can include one or a plurality of rollers that can support and guide the one or a plurality of supporting materials 312 or, as illustrated in FIG. 15, the bottom of each of the one or a plurality of supporting materials 312 can hang freely in a substantially vertical configuration. The one or a plurality of supporting materials 312 can be rotated into contact with the contacting liquid 314, which can allow the algal cells 318 to attach to the one or a plurality of supporting materials 312. The drive motor 324 can include a gear system 326 or pulley system that can drive the one or a plurality of drive shafts 328, where the one or a plurality of drive shafts 328 can rotate the one or a plurality of supporting materials 312 into and out of the contacting liquid 314. Embodiments can also include a trough system 330, mister, water dripper, or any other suitable component or mechanism that can keep algae, which can be attached to the one or a plurality of supporting materials 312, moist. Embodiments can include any suitable scraping system, vacuum system or mechanism for harvesting the algal cells 318 from the one or a plurality of supporting materials 312. It will be appreciated that the drive motor 324 can be associated with a plurality of mechanized harvesting units 322 or one or a plurality of supporting materials 312. In an alternate embodiment, each of the one or a plurality of supporting materials 312 can be associated with an independent motor, gear, and/or drive shaft system (not shown). It may be efficient to operate one or more of the one or a plurality of supporting materials 312 on the same schedule, but it may also be advantageous to operate some or all of the one or a plurality of supporting materials 312 on different schedules. For example, in one embodiment, a supporting material exposed to natural light can be associated with a light sensor (not shown) and controller (not shown) such that the rotation speed of the supporting material is optimized relative to the available light. In such an example, one or a plurality of supporting materials in the same facility may have different, or slightly different environmental conditions, where operating each one or a plurality of supporting materials independently may substantially optimize the overall system.

The mechanized harvesting unit 322 can have a generally vertically-shaped configuration of one or a plurality of supporting materials 312 that can be supported by the frame 323. It will be appreciated that the frame 323 can be constructed from any suitable material, such as metal, and can have any suitable configuration in accordance with embodiments described herein. Each of the one or a plurality of supporting materials 312 can be a contiguous band of material, strips, ropes, slats, ribbons, plates, scales, overlapping material, or the like, and can be wound about the one or a plurality of drive shafts 328 or rollers (not shown) such that any suitable configuration can be created. It is contemplated that the supporting material can be a long, contiguous band of material having multiple peaks and valleys, or can be separate units as illustrated in FIG. 15. It will be appreciated that a single long band and a plurality of bands having any suitable relationship or configuration are contemplated.

Figure 17:
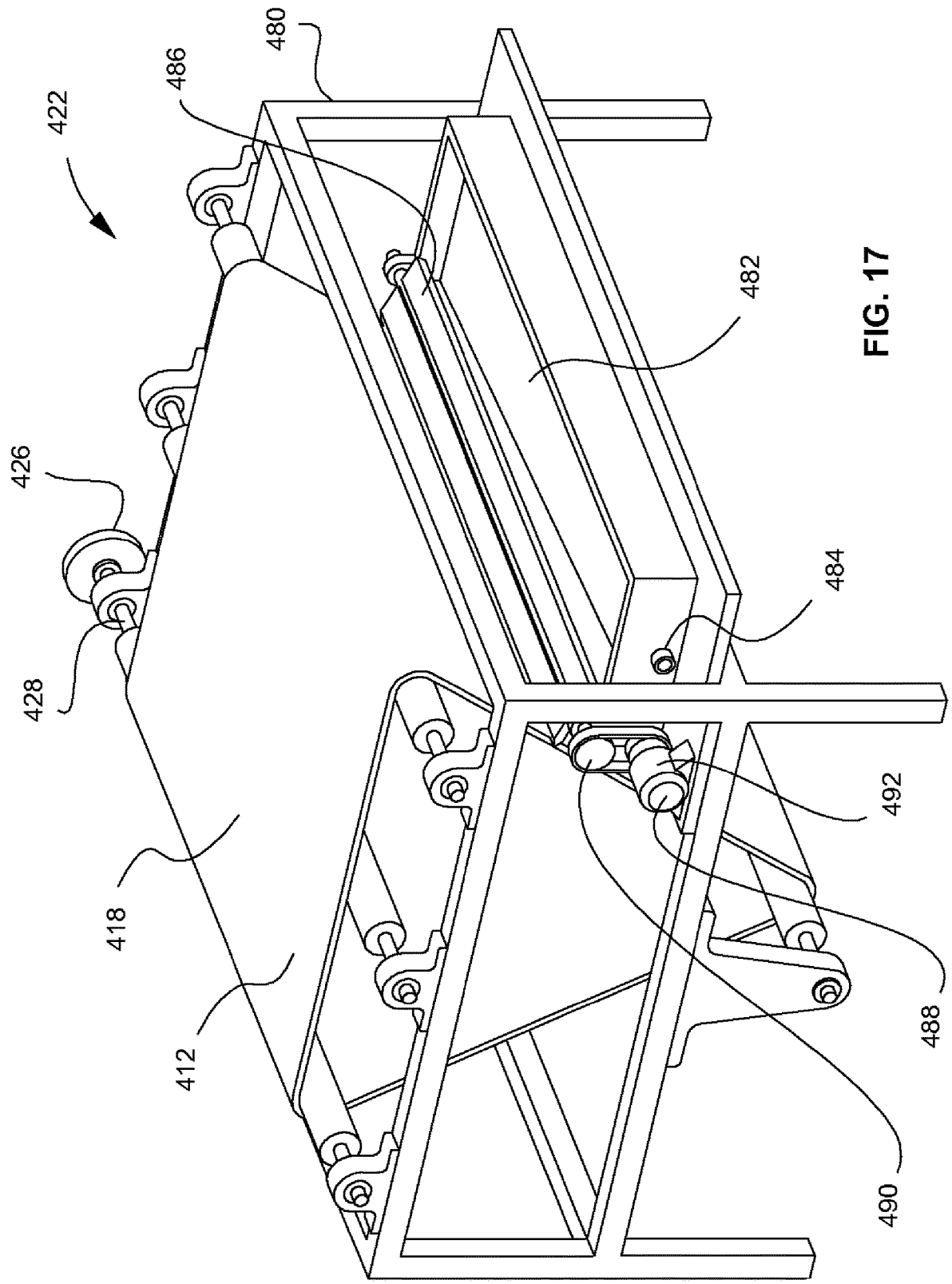
FIG. 17 depicts a perspective view of an algal growth system shown with a harvesting system according to one embodiment.

Referring to FIG. 17, an example embodiment of an algal growth system or mechanized harvesting unit 422 is shown, in which algal cells 418 can be attached to a solid surface of a supporting material 412. Embodiments of the mechanized harvesting unit 422 can include a drive motor (not shown), and a gear system 426 that can rotate one or a plurality of drive shafts 428, where the one or a plurality of drive shafts 428 can correspondingly rotate the supporting material 412, such as a flexible sheet material. Embodiments of the mechanized harvesting unit 422 can include a harvesting system 480 that can include any suitable manual or automatic harvesting mechanism and/or a harvesting reservoir 482. The harvesting system 480 can include a vacuum system 484 and a scraper 486 for harvesting the algal cells 418 from the supporting material 412. The scraper 486 can be coupled with a motor 488 and a pulley system or actuator 490 such that the scraper 486 can be selectively engaged with the supporting material 412. The motor 488 can be associated with a controller 492 such that the harvesting system 480 can be programmed to scape, harvest, or perform any other suitable function automatically or on a predetermined schedule.

Figure 20:
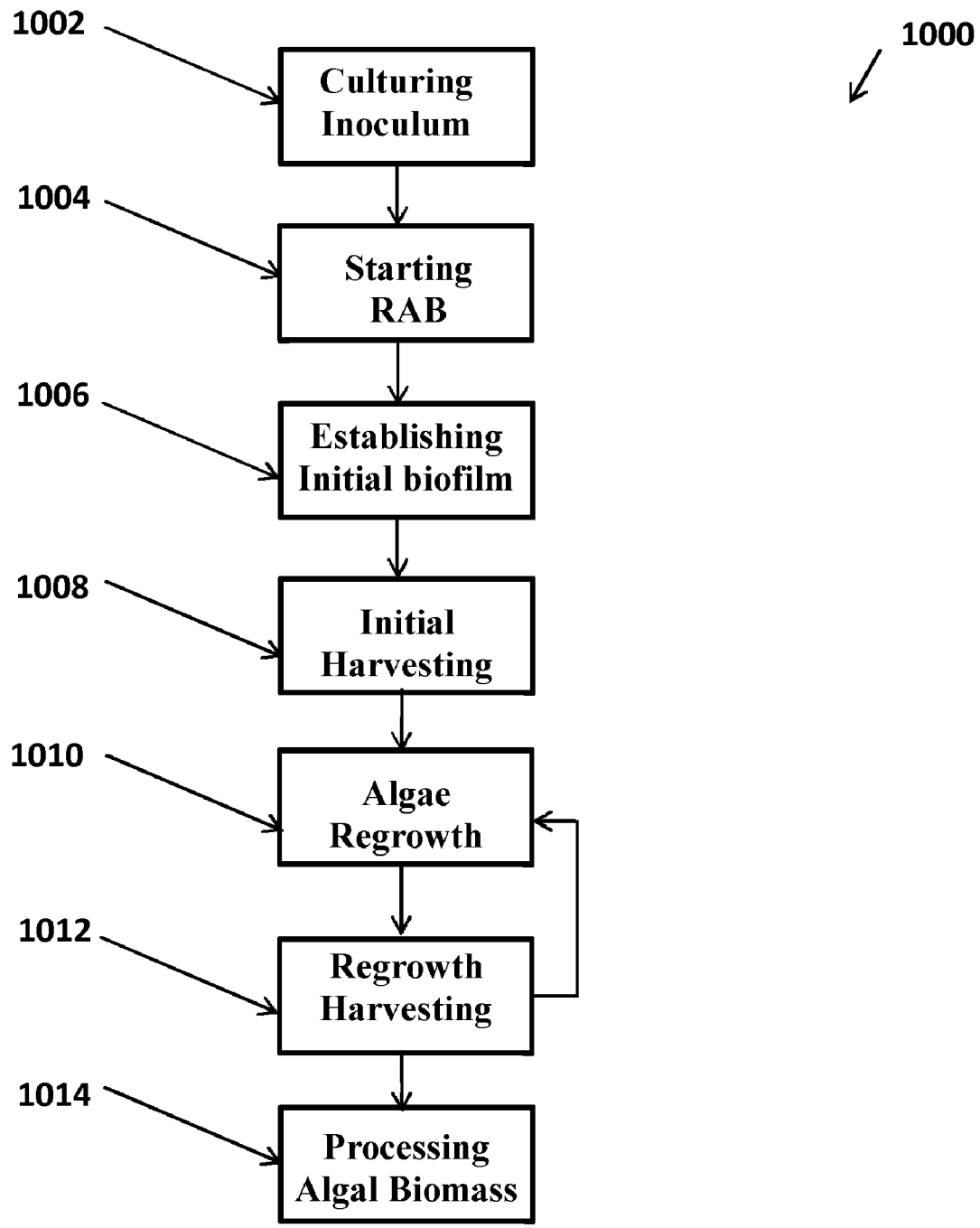
FIG. 20 depicts a flow chart showing a method for growing and harvesting algae using a raceway according to one embodiment.

FIG. 20 depicts a flow chart illustrating one example of a method 1000 that can be used for growing and/or harvesting algal cells using a raceway, such as the raceway 130 shown in FIGS. 9 and 11. The method 1000 can include Culturing Algal Inoculum 1002, which can include culturing suspended algae in an open pond, raceway, or the like, until the algal cell density is between from about 0.05 g/L to about 1.0 g/L. It will be appreciated that any suitable density of any suitable algal cells is contemplated. The method 1000 can include Starting the RAB 1004, which can include rotating or actuating the supporting material of a photobioreactor, algal growth system, mechanized harvesting unit, or the like, in accordance with versions described herein. The RAB or other suitable system can be rotated, for example, at a speed ranging from about 4 cm/sec to about 10 cm/sec. The RAB can be rotated at from about 2 cm/sec to about 6 cm/sec. The RAB can be rotated at about 4 cm/sec. The RAB can be rotated or otherwise actuated at different speeds, which can be selectable, preprogrammed, or based on environmental conditions. Starting the RAB 1004 can include rotating the RAB system for any duration of time such as from about 5 days to about 20 days, where duration of operation can depend on the speed of the algal cells attachment on the surface of the RAB materials.

The method 1000 can include Establishing Initial Biofilm 1006, which can include the growth of algal cells on the supporting material of an RAB or photobioreactor. The initial biofilm can be deemed to be established when, for example, a threshold density of algal cells is determined. Such a threshold can be any suitable density and the density can be determined using any suitable system or method. The method 1000 can include Initial Harvesting 1008, which can include harvesting the algal biomass from the supporting material of the RAB or photobioreactor. Initial Harvesting 1008 can be accomplished by scraping the algal biofilm, vacuuming, pressurized air, or by any other suitable method.

The method 1000 can include Algae Regrowth 1010, where after harvesting, residual algal cells can remain on the supporting material surface and can automatically serve as inoculum for a next cycle of growth or regrowth. Harvesting can be performed such that a sufficient density of algal cells can be left on the supporting material to facilitate regrowth. Algae Regrowth 1010 can include operating, actuating, or rotating the algal biofilm, RAB, or photobioreactor for any suitable time period such as from about 3 days to about 8 days. The time for operating the RAB can depend, for example, on the algal species, culture conditions, rotating speed of the RAB system, the liquid fluid rate reservoir, or any other suitable factor. Method 1000 can include Regrowth Harvesting 1012, which can include harvesting the algal biofilm that has accumulated on the supporting material. The method 1000 can include repeating Algae Regrowth 1010 and Regrowth Harvesting 1012 for as many times as appropriate. The system can operate substantially indefinitely, or can be periodically interrupted for cleaning or for other reasons. The method 1000 can include Processing Algal Biomass 1014, which can include processing the harvested algae by, for example, drying and extracting oil from the harvested algal cells. It will be appreciated that any suitable processing is contemplated.

Figure 19:
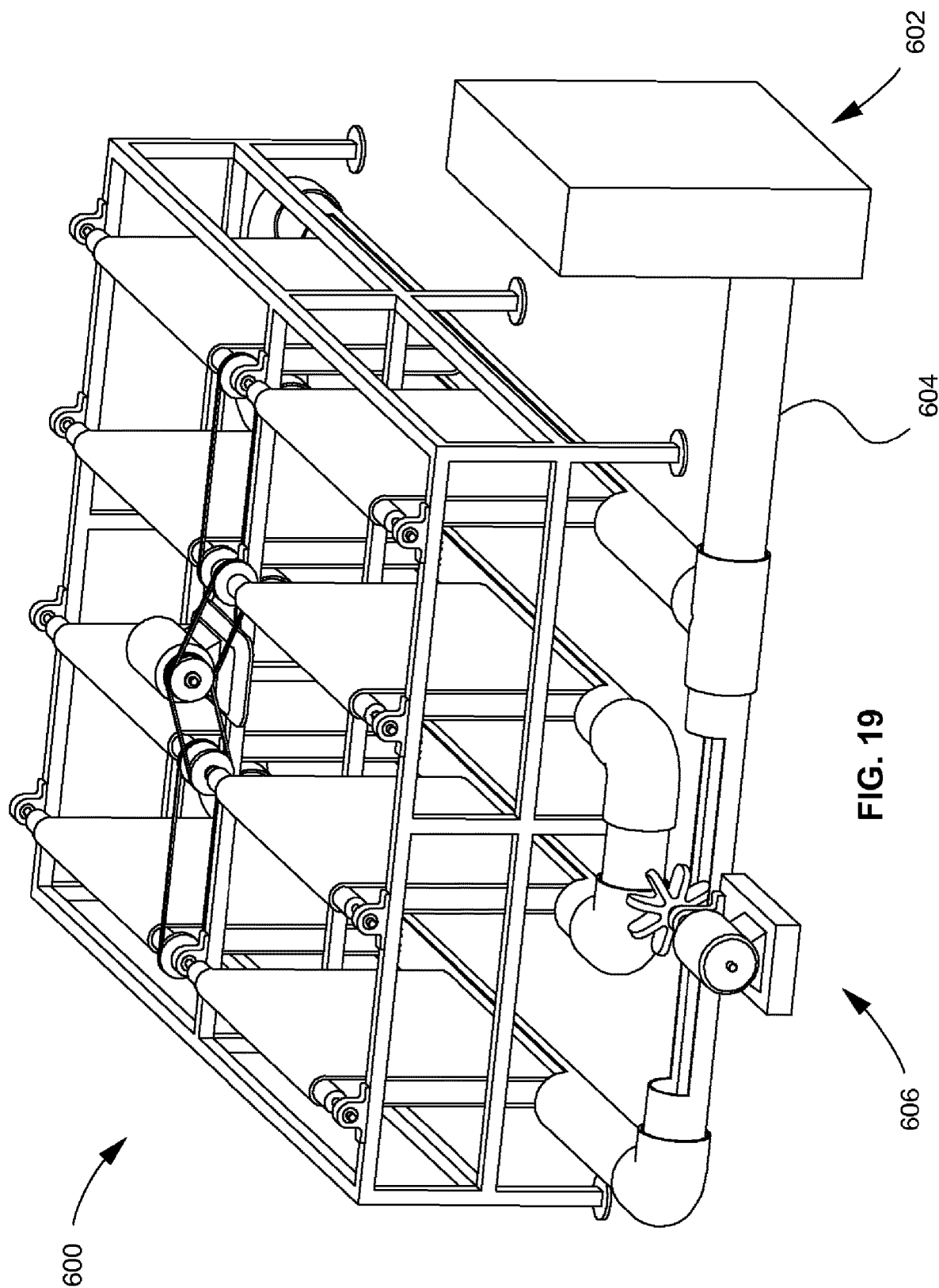
FIG. 19 depicts a perspective view of a photobioreactor according to one embodiment.
Figure 21:
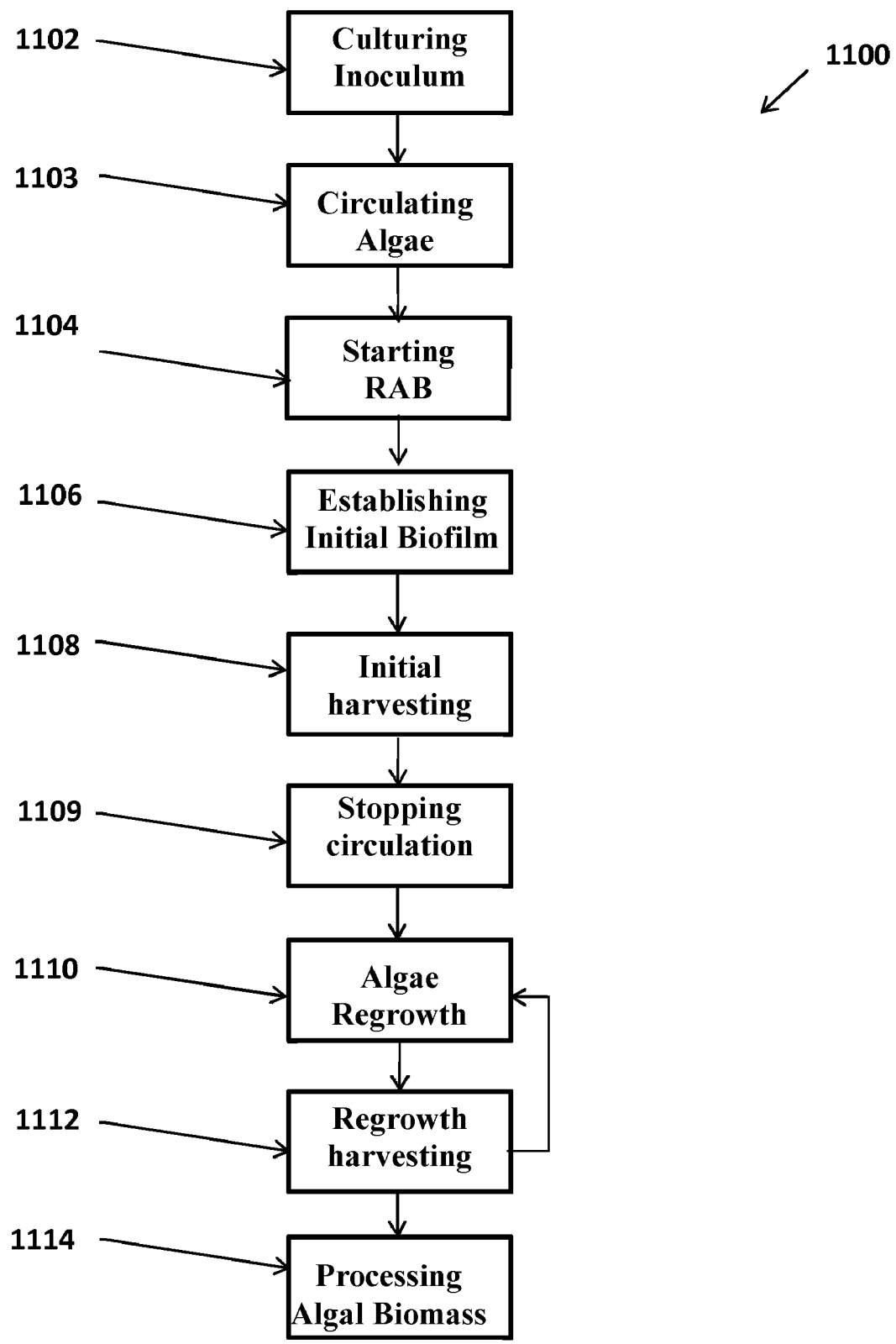
FIG. 21 depicts a flow chart showing a method for growing and harvesting algae using a trough according to one embodiment.

FIG. 21 depicts a flow chart illustrating one example of a method 1100 that can be used for growing and/or harvesting algal cells, such as with a photobioreactor 600 shown in FIG. 19, a trough, a partially enclosed fluid reservoir, or other suitable bioreactor. In such a system, it may be beneficial to seed or otherwise provide algal cells grown at a first location 602 (FIG. 19) and transport the algal cells via a channel 604 (FIG. 19), or other suitable connection, to a second location 606 (FIG. 19), such as to a photobioreactor provided in accordance with versions described herein. The first location can be fluidly coupled to the second location or, in an alternate embodiment, the first location can be a portable bioreactor that can be selectively connected to the second location as needed.

The method 1100 can include Culturing Algal Inoculum 1102, which can include culturing suspended algae in an open pond, portable photobioreactor, or the like, at the first location until the algal cell density is between, for example, from about 0.05 g/L to about 3.0 g/L. It will be appreciated that any suitable density of any suitable algal cells is contemplated, although in one embodiment the cell density can be higher than in an open raceway system, where the reduction of light in a trough system may benefit from a higher initial cell density. The method 1100 can include Circulating Algae 1103, which can include providing or otherwise delivering the algal cells from the first location to the trough or partially enclosed system, which can include generating a fluid dynamic or flow such that algal cells from the first growth region are transitioned to the trough in the second region. The method 1100 can include Starting the RAB 1104, which can include rotating or actuating the supporting material of a photobioreactor, algal growth system, mechanized harvesting unit, or the like, in accordance with versions described herein. The RAB or other suitable system can be rotated, for example, at a speed ranging from about ¼ cm/sec to about 10 cm/sec. The RAB can be rotated at from about 2 cm/sec to about 6 cm/sec. The RAB can be rotated at about 4 cm/sec. The RAB can be rotated or otherwise actuated at different speeds, which can be selectable, preprogrammed, or based on environmental conditions. Starting the RAB 1104 can include rotating the RAB system for any duration of time such as from about 5 days to about 20 days, where duration of operation can depend on the speed of the algal cells attachment on the surface of the RAB materials.

The method 1100 can include Establishing Initial Biofilm 1106, which can include the growth of algal cells on the supporting material of an RAB or photobioreactor. The initial biofilm can be deemed to be established when, for example, a threshold density of algal cells is determined. Such a threshold can be any suitable density and the density can be determined using any suitable system or method. The method 1000 can include Initial Harvesting 1108, which can include harvesting the algal biomass from the supporting material of the RAB or photobioreactor. Initial Harvesting 1008 can be accomplished by scraping the algal biofilm, vacuuming, pressurized air, or by any other suitable method.

The method 1100 can include Stopping Circulation 1109, which can include stopping delivery of algal cells from the first growth location to the second trough location, for example. In one embodiment, once the RAB is seeded with algal cells, the RAB may no longer need to be seeded or otherwise infused with additional algal cells for subsequent regrowth and harvesting steps. It will be appreciated that a feeder or seeding system for algal cells can be reattached or can be maintained throughout if desirable. The method 1100 can include Algae Regrowth 1110, where after harvesting, residual algal cells can remain on the supporting material surface and can automatically serve as inoculum for a next cycle of growth or regrowth. Harvesting can be performed such that a sufficient density of algal cells can be left on the supporting material to facilitate regrowth. Algae Regrowth 1110 can include operating, actuating, or rotating the algal biofilm, RAB, or photobioreactor for any suitable time period such as from about 3 days to about 30 days, about 3 days to about 8 days, or longer than 30 days. The time for operating the RAB can depend, for example, on the algal species, culture conditions, rotating speed of the RAB system, the liquid fluid rate of the reservoir, the type of reservoir, or any other suitable factor. Method 1100 can include Regrowth Harvesting 1112, which can include harvesting the algal biofilm that has accumulated on the supporting material. The method 1100 can include repeating Algae Regrowth 1110 and Regrowth Harvesting 1112 for as many times as appropriate. The system can operate substantially indefinitely, or can be periodically interrupted for cleaning or for other reasons. The method 1100 can include Processing Algal Biomass 1114, which can include processing the harvested algae by, for example, drying and extracting oil from the harvested algal cells. It will be appreciated that any suitable processing is contemplated.

Example systems and methods can include developing a biofilm-based microalgae cultivation system (RAB) that could be widely adapted by the microalgae industry for producing, for example, fuels and high value products, as well as for treating municipal, industrial, and agricultural wastewater. Microalgae use photosynthesis to transform carbon dioxide and sunlight into energy. This energy is stored in the cell as oil, which has a high energy content. The oil yield from algae can be significantly higher than that from other oil crops. Algae oil can generally be easily converted to biodiesel and could replace traditional petroleum-based diesel. In addition to fuel production, microalgae have also been rigorously researched for the potential to produce various high value products such as animal feed, omega-3 polyunsaturated fatty acids, pigments, and glycoproteins.

Another example application for a biofilm-based microalgae cultivation system (RAB) that could be widely adapted by the microalgae industry is for treating municipal, industrial, and agricultural wastewater. Specifically, systems and methods may include reducing total dissolved solids (TDS) in wastewater by an algal biofilm treatment such as by using a continuous revolving algal biofilm reactor. Total dissolved solids (TDS) comprising various inorganic salts (e.g., chloride, calcium, magnesium, potassium, sodium, bicarbonates, and sulfates) and organic compounds is emerging as toxic pollutants to human and aquatic systems. Human activities such as agriculture, water use and treatment, urbanization, de-icing salt applications, and mining can significantly exacerbate the TDS level in surface and ground waters. Compared to the existing TDS removal methods (e.g., physical adsorption, reverse osmosis, distillation, membrane filtration, and bacteria-based bioremediation), biological absorption by microalgae is a mild and environmental friendly method for TDS removal. Algal cells absorb TDS species as nutrients and minerals to support their physiology and metabolisms while reducing TDS in water.

An example embodiment of a method of reducing TDS in wastewater by an algal biofilm treatment includes inducing the biofilm to produce extracellular polymeric substances (EPS)—a 3-D polymer network to facilitate algal cells to adhere on the belt and interact each other—using the revolving algal biofilm system in which an algal biofilm moves between the wastewater and a gas phase. In particular, the negatively charged functional groups (e.g., carboxyl, hydroxyl, and phosphoric groups) in the EPS can adsorb various salts and organic matters. When used to treat wastewater with high TDS content, the polysaccharides in EPS have a very high binding capacity. This physically-based adsorption, together with the biological assimilation by the biofilm cells, enables the RAB system to remove a wide spectrum of dissolve solids from the wastewater.

The method may include, for example, increasing the EPS production by stressing the algae in the algal biofilm systems. Correspondingly, the system may include a stressor that is operably configured to stimulate the algae to produce an extracellular polymeric substance. In general, EPS is produced as a response to algal cells' defense mechanisms against abiotic or biotic stresses or is enhanced by manipulations of the stressors. Algae have evolved to grow in water or very damp conditions, and bringing algal cells outside of the water in the revolving algal biofilm system triggers the defense mechanism to produce EPS to resist dehydration of algal cells. Example stressors include, without limitation, changes in pH (e.g., increasing the pH of the algal biofilm; decreasing the pH of the algal biofilm), changes in temperature (e.g., increasing the temperature of the algal biofilm; decreasing the temperature of the algal biofilm; modulating the temperature of the algal biofilm), exposing the algal biofilm to a gas phase, time spent outside of the wastewater, ratio of time in wastewater vs. out of wastewater (i.e., gas vs. liquid phase), adjusting the amount of light applied to the algal biofilm (e.g., using a dark cycle), and adjusting the wavelength of the light applied to the algal biofilm. Additionally or alternatively, a compound configured to increase the production of EPS may be added to the biofilm support or to the wastewater itself. The revolving algal biofilm system can have a height ranging from, for example, 1-ft to 30-ft tall. The gas/liquid phase ratio can range from, for example, 0.2% (1:500) to 50% (1:2). In an embodiment, the speed of rotating of the algal biofilm can be from 0.1 cm/sec to 100 cm/sec.

The method may include promoting the selective growth of algae that produces a greater amount of EPS. In other words, the EPS production varies based on the algae species in the algal biofilm. Green alga species for high EPS production include, without limitation, *Chlorella Vulgaris, Chlorella ellipsoidea, Chlamydomonas* sp., *Botryococcus braunii*, and *Dunaliella salina*.

Additionally, or alternatively, an example embodiment of a method of reducing TDS in wastewater by an algal biofilm treatment includes precipitating salts on the algal biofilm or supporting material using the RAB system. For example, abiotic salts may precipitate on the surface of the algal biofilm or supporting material. The system may be adjusted to increase such precipitation. For example, increasing or decreasing the pH of the wastewater may facilitate precipitation of the ions. This chemical precipitation, along with the physically-based adsorption by EPS and biological assimilation by the biofilm cells, enables the RAB system to remove a wide spectrum of dissolve solids from the wastewater.

The following examples are provided to help illustrate the present technology, and are not comprehensive or limiting in any manner.

Example 1

Wastewater Streams. Four types of wastewaters representing industrial effluents and municipal wastewater were used. These wastewaters include (i) synthetic industrial effluent with low TDS strength (Industry WW/low TDS), (ii) synthetic industrial effluent with high TDS strength (Industry WW/high TDS), (iii) municipal wastewater (primary effluent after solids being screened out but before entering the 1st sedimentation basin) from Ames water pollution control plant in Ames, IA, USA (Ames WW), and (iv) Ames WW supplemented with sodium chloride (Ames WW+NaCl). The compositions of those wastewaters and preparation methods are provided in Table 1.

TABLE 1

| | Wastewater (WW) sources | | | |
|---|---|---|---|---|
| Components (mg/L) | Low-TDS Industrial WW | High-TDS Industrial WW | Ames WW | Ames WW + NaCl |
| Sodium | 417 | 1,601 | 88 | 425 |
| Potassium | 64 | 252 | 13 | 13 |
| Calcium | 368 | 1,359 | 80 | 79 |
| Magnesium | 97 | 324 | 17 | 16 |
| Chloride | 1,250 | 4,500 | 175 | 781 |
| Sulfur | 138 | 540 | 33 | 37 |
| Nitrogen | 14 | 56 | 26 | 26 |
| Phosphorus | 9 | 36 | 12 | 13 |
| Silicon | 23 | 92 | Not added | Not added |
| BBM trace metals stock solutions | 10 mL/L | 10 mL/L | Not added | Not added |

The Low-TDS industrial WW was prepared by dissolving 1,000 mg/L NaCl, 1,000 mg/L $CaCl_2$, 100 mg/L $KNO_3$, 500 mg/L $MgSO_4$, 100 mg/L $NaSiO_3$, 50 mg/L $K_2HPO_4$ and 10 mL/L Bold's Basal Medium (BBM) trace metal stock solution into water. The composition of the BBM trace metal stock solution includes 97 mg/L $FeCl_3 \cdot 6H_2O$, 41 mg/L $MnCl_2 \cdot 4H_2O$, 5 mg/L $ZnCl_2$, 2 mg/L $CoCl_2 \cdot 6H_2O$ and 4 mg/L $Na_2MoO_4 \cdot 2H_2O$. The High-TDS industrial WW has the same component species at a concentration of four times the concentration of those in Low-TDS industrial WW. The Ames WW+NaCl was prepared by adding 1,000 mg/L sodium chloride into Ames WW.

The Industry WW with high TDS and low TDS were used to mimic industrial effluents. The salts concentration in these two effluents was prepared based on data commonly recorded by the Metropolitan Water Reclamation District (MWRD) of Greater Chicago. The Ames WW+NaCl mimicked the municipal wastewater with high salt content.

Microalgae Seed Cultures. A microalgal seed culture (0.5-1 g/L of biomass, dry basis) was maintained at a raceway pond (1,000 L working volume) at the Algal Production Facility at Iowa State University in Boone, IA, USA. The culture has been maintained using Bold's Basal Medium (BBM) with half of the raceway pond culture being exchanged with fresh medium every 7 days. The pond has been operated for four years and a stable community containing various green algae, diatom and cyanobacteria species with minimal amount of prokaryotes bacteria and eukaryotic fungus has been established over the year of subculture.

RAB System Design and Operation. A flexible cotton duct canvas belt was stretched around drive shafts to form a vertical configuration. The lower region (about 10%) of the belt was submerged in a liquid reservoir (1.2 L working volume) to supply nutrients, while the rest of the belt was exposed to the air to access light irradiation. The shafts were driven by a motor at speed of 4 cm/sec to rotate the belt between the liquid and gas phases. To initiate cell attachment on the RAB belt, the liquid reservoir was inoculated with the algal seed culture and the RAB belt was rotated under continuous illumination of 110-120 μmol photons m−2 s−1 at 25° C. The suspended algal cells gradually attached on the RAB belt over a period of 2-3 weeks, during which the reservoir was supplemented with additional seed culture to compensate for water evaporative loss. After initial attachment the algal biomass was harvested by scraping and the residual colonies remained on the material served as inoculum for the next growth cycle.

Each wastewater stream was used as the influent to feed the RAB liquid reservoir, with the equal volume of the effluent being discharged. The effluent discharge/influent feeding was operated on daily basis with a hydraulic retention time (HRT) of 1 day and 3 days, respectively. The effluent discharged from the liquid reservoir was centrifuged at 5,000 rpm at 4° C. for 5 min to remove the solid residual; the supernatant was immediately analyzed for TDS and chloride concentrations. The remaining supernatant was stored at −20° C. for further analyzing salt concentrations. The biomass was harvested by scraping the biofilm from the RAB belt every 6 days. The harvested biomass was freeze-dried to determine the cell dry weight, and then stored for further analysis of ions contents.

Comparative Bubble Column Design and Operation. Suspended cultures on bubble column (BC) reactors were also performed as a comparison baseline for the RAB system. The BC reactors were made from Pyrex glass with an inner diameter of 6.5 cm and a height of 50 cm. Each column had a working volume of 1.2 L. The BC reactor was inoculated with 1.2 L seed cultures. The HRT was set at 3 days, i.e., 400 ml of effluent was discharged from the reactor and same amount of influent was fed on daily basis. Modified BBM medium, as described by Orosa et al., "Production and analysis of secondary carotenoids in green alga," Journal of Applied Phycology 12:553-556 (2000), was used as influent to the reactor in the first six days of operation to ensure the system reached a steady state; then, the feeding influents were switched to the different wastewaters as described above. During the continuous operation, the optical density of the cell suspension in the discharged effluent was determined at 680 nm ($OD_{680}$) on daily basis and then converted into dry cell weight concentration based on the linear relationship between $OD_{680}$ and cell concentration. Then, the effluent discharged from the BCs was centrifuged to separate cell suspension into supernatant and biomass pellets. The supernatant was stored for analysis of TDS, chloride, and salt concentrations. The cell pellet was freeze-dried and stored for further analysis of ash and ions contents. During the operation, the BCs were aerated with air at 1.0 L/min under continuous illumination of 110-120 $\mu m^{-2} s^{-1}$ light intensity at 25° C.

Determination of TDS, Chloride, and Other Ions Concentrations in Liquid. TDS and chloride concentrations were determined by Multi-Parameter PCSTesr 35 (Oakton, CA, USA) and Chloride Test kits (Hach, CO, USA), respectively. The concentrations of the sodium, potassium, calcium, magnesium, and sulfur were determined by an iCAP 7400 inductively coupled plasma-optical emission spectrometry (ICP-OES; Thermo Scientific) with the program Qtegra (Version 2.7.2425.65, Thermo Scientific). Nitric acid (2%) was used as rinse solution. Yttrium ICP standard (5 ppm) and IV-ICPMS-71A (Inorganic, USA) were used as the internal standard and elemental standards, respectively. The wavelength used for sodium, potassium, calcium, magnesium and sulfur were 589 nm, 766 nm, 315 nm, 279 nm, and 180 nm, respectively. The analytical wavelength was chosen based on EPA-METHOD 6010 C and the elemental standards.

Determination of Ash and Ion Contents in Biomass. The ash content of biomass was determined by heating the biomass at 550° C. for 6 h. To analyze the contents of various elements, 5 mL nitric acid were used to digest about 20 mg dry biomass in an Anton-Paar Multiwave GO system with a 30 min-long microwave program (10-min ramp to reach a power of 1200 W, followed with 10-min at 1200 W and 180° C. and then 10-min cooling). Digested samples were diluted with deionized water into 50 mL, which were then analyzed for elemental composition using ICP-OES. The biomass contents of these elements were calculated based on the element concentrations in the digested liquid and the biomass dry weight.

Determination of EPS Compositions in Algal Biomass. The biomass harvested from the RAB and BC reactors were rinsed twice with distilled water and treated with sonication to extract the EPS. The cell pellet was suspended in 20 ml of phosphate buffer solution (10 mM NaCl, 1.2 mM $KH_2PO_4$, and 6 mM $Na_2HPO_4$) at a concentration equivalent to 1 g/L (dry basis). The cell pellet solution was placed in an ice bath and EPS was extracted with a Model 500 Sonic Dismembrator (Fisher Scientific, USA) at 40% sonication intensity for 2 min. The samples were then centrifuged at 9,000 rpm for 15 min, and the supernatant containing EPS was collected. The protein and polysaccharide concentrations in the supernatant solution were determined by Total Protein Kits (Sigma, USA) and based on the method reported by Dubois et al. (1956), respectively. These concentration data (mg/L) were then converted into the cellular content of the protein and the polysaccharide (mg/g dry biomass) based on the volume of the supernatant and the equivalent biomass dry weight. Total EPS content was determined by combining the protein and polysaccharide contents.

Results. The experimental data were analyzed through one-way ANOVA. The F value and P values were determined, and a P value of less than 0.05 was regarded as significant.

Figure 22:
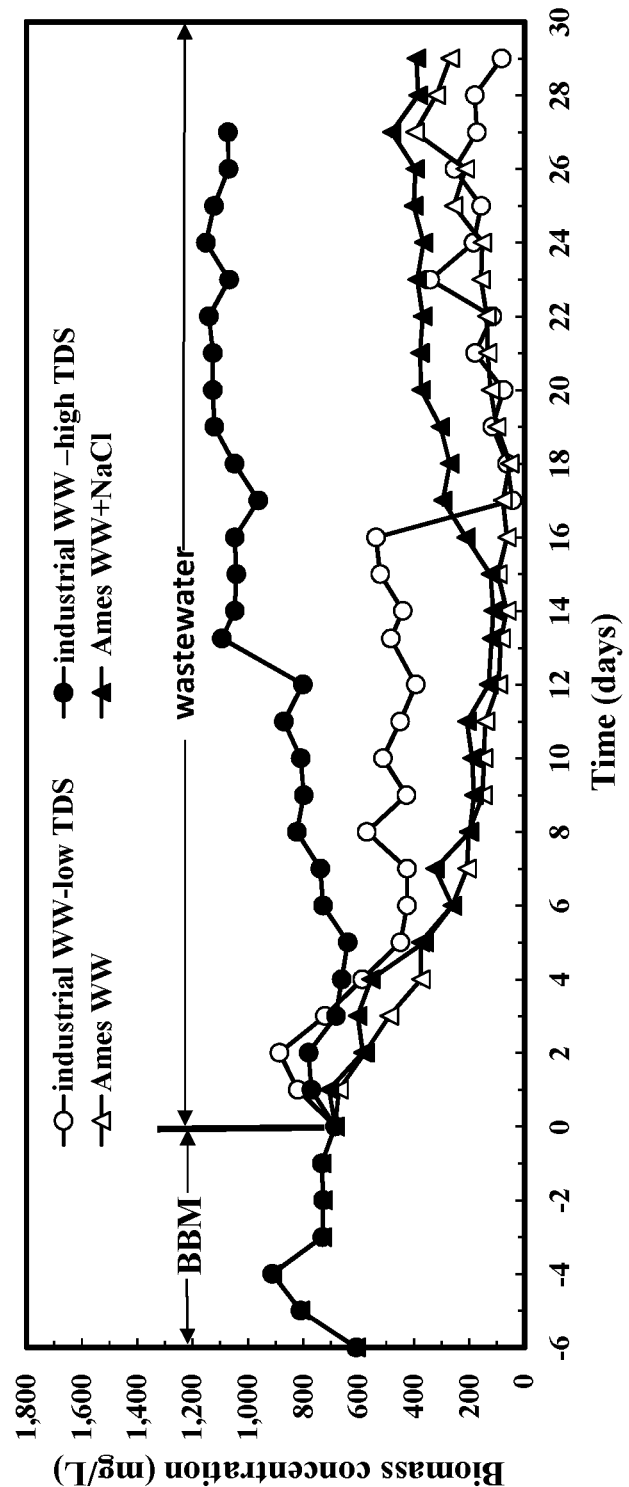
FIG. 22 depicts a graph of biomass concentration of polyculture each day in bubble column reactors fed with the following wastewater (WW) sources: low-TDS industrial WW (○); high-TDS industrial WW (•); Ames WW (▲); and Ames WW+NaCl (Δ).
Figure 24A:
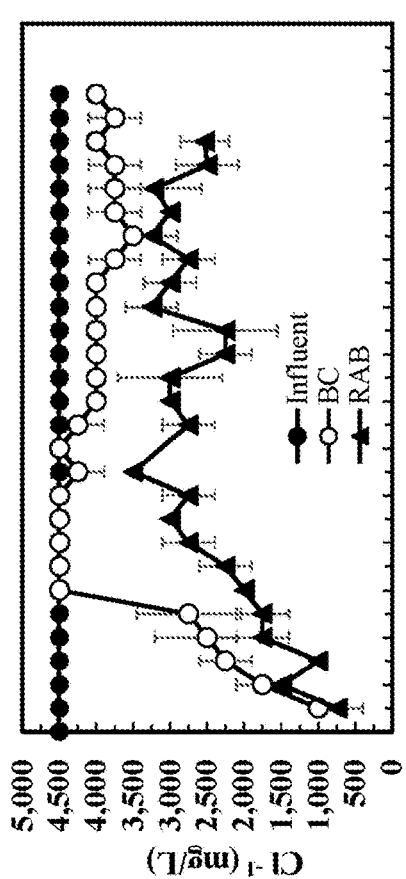
FIG. 24A depicts the concentration of chloride in the influent and effluent during the continuous operation of the RAB and BC reactors fed with a wastewater (WW) source of low-TDS industrial WW.
Figure 24B:
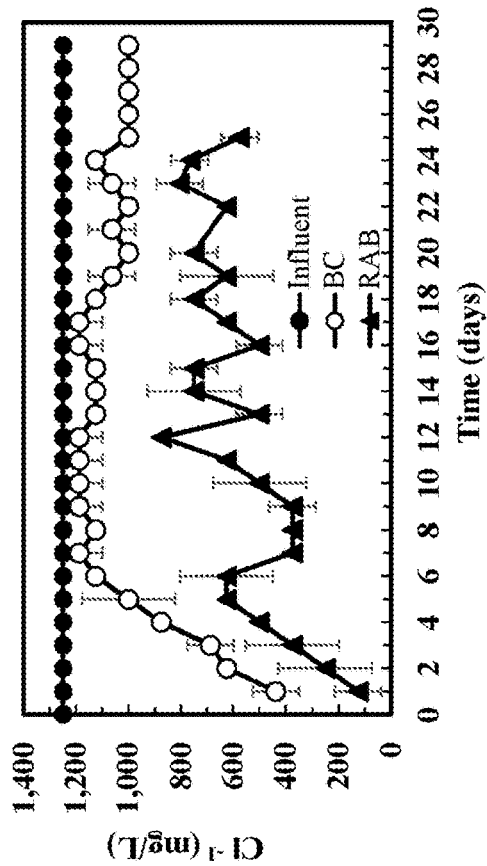
FIG. 24B depicts the concentration of chloride in the influent and effluent during the continuous operation of the RAB and BC reactors fed with a wastewater (WW) source of high-TDS industrial WW.
Figure 24C:
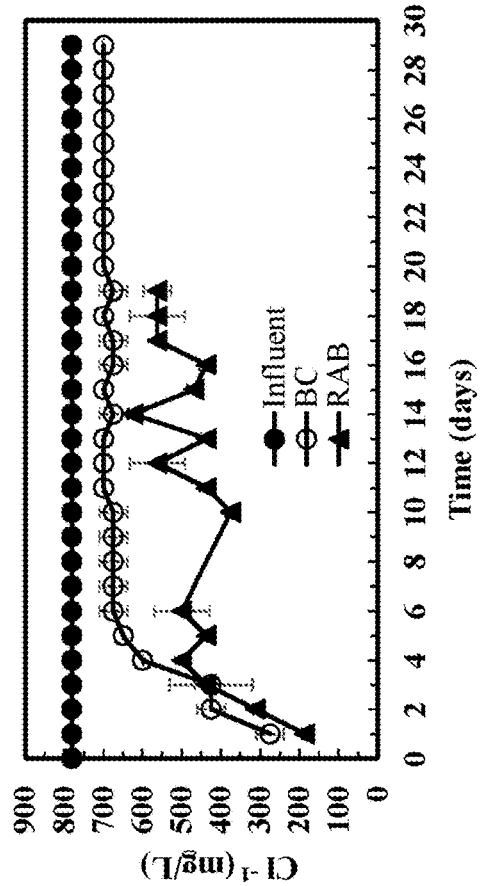
FIG. 24C depicts the concentration of chloride in the influent and effluent during the continuous operation of the RAB and BC reactors fed with a wastewater (WW) source of Ames WW.
Figure 24D:
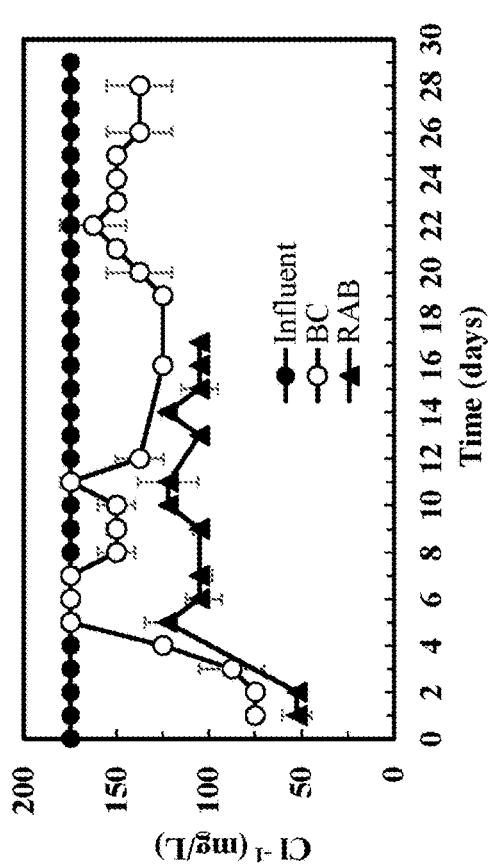
FIG. 24D depicts the concentration of chloride in the influent and effluent during the continuous operation of the RAB and BC reactors fed with a wastewater (WW) source of Ames WW+NaCl.

Microalgae Growth and Ash Contact in BC and RAB Reactors. The algal growth performance in BC reactors fed with different wastewaters was evaluated. FIG. 22 shows the daily change of ash-containing biomass density in continuous culture over 30 days of operation. All the reactors were fed with BBM medium in the first six days and then switched to the different wastewater streams as the influent. The cell growth was fluctuated in the first 18-20 days before reaching the quasi steady state. The reactor was operated at 3-day of HRT. The steady state biomass concentration in High-TDS industrial WW reached around 1,100 mg/L, higher than the other three types of wastewaters. The cell growth in the other three wastewaters was similar, without significant difference.

The biomass productivity ($P_{BC}$) in BCs was determined as follows, $$P_{BC} = \frac{C}{HRT} \quad (1)$$

where C is the biomass concentration (mg/L), and HRT is set at 3 days. Productivities based on ash-containing and ash-free biomass were determined. Table 2 shows the productivity and ash content of the biomass produced from bubble column reactors fed with the different wastewater sources.

TABLE 2

| Wastewater sources | Ash-containing biomass productivity (mg DW/L-day) | Ash content (%) | Ash-free biomass productivity (mg AFDW/L-day) |
|---|---|---|---|
| Low-TDS Industrial WW | 126 ± 16.66 | 30.91 ± 3.88 | 87 ± 11.51 |
| High-TDS Industrial WW | 304 ± 22.86 | 65.29 ± 0.94 | 106 ± 7.94 |
| Ames WW | 97 ± 14.71 | 22.79 ± 2.24 | 75 ± 11.36 |
| Ames WW + NaCl | 110 ± 16.07 | 14.79 ± 1.70 | 94 ± 13.69 |

The industrial WW with high TDS resulted in the highest productivity for both ash-containing biomass and ash-free biomass. The other three types of wastewater had similar biomass productivity. The ash content of the biomass derived from the industrial WW with high TDS was the highest due to the high salt concentration in this type of wastewater.

The algal growth in RAB reactors fed with different wastewater streams was also evaluated. The attachment surface based biomass productivity was determined as follows, $$P_{RAB} = \frac{DW}{B \times F} \quad (2)$$

where $P_{RAB}$ is surface based biomass productivity (mg/$m^2$-day), DW is the dry weight (mg) of biomass harvested from the RAB belt, B is the surface area of the attachment belt (0.171 $m^2$), and F is the frequency of harvesting biomass (six days).

The biomass productivity and ash content of the biomass produced from RAB reactors at 1-day HRT (RAB-1) and RAB at 3-day HRT (RAB-3), fed with different wastewater sources, are shown in Table 3.

TABLE 3

| Wastewater sources | Ash-containing biomass productivity (mg DW/$m^2$-day) | | Ash content (%) | | Ash-free biomass productivity (mg AFDW/$m^2$-day) | |
|---|---|---|---|---|---|---|
| | RAB-1 | RAB-3 | RAB-1 | RAB-3 | RAB-1 | RAB-3 |
| Low-TDS Industrial WW | 527 ± 3.24 | 596 ± 127 | 30.58 ± 1.92 | 25.07 ± 6.62 | 366 ± 2.25 | 446 ± 97.0 |

TABLE 3-continued

| Wastewater sources | Ash-containing biomass productivity (mg DW/m²-day) | | Ash content (%) | | Ash-free biomass productivity (mg AFDW/m²-day) | |
|---|---|---|---|---|---|---|
| | RAB-1 | RAB-3 | RAB-1 | RAB-3 | RAB-1 | RAB-3 |
| High-TDS Industrial WW | 2,549 ± 4.70 | 2,556 ± 300 | 61.69 ± 10.52 | 52.29 ± 0.54 | 977 ± 3.82 | 1,219 ± 143 |
| Ames WW | 623 ± 137 | 595 ± 131 | 20.22 ± 3.12 | 14.10 ± 5.44 | 497 ± 109 | 511 ± 112 |
| Ames WW + NaCl | 600 ± 130 | 553 ± 92.7 | 21.51 ± 6.75 | 17.18 ± 4.94 | 471 ± 101 | 458 ± 92.5 |

Among four different wastewaters, High-TDS industrial WW resulted in ash-containing biomass productivities of 2,549 mg/m²-day (1-day HRT) and 2,556 mg/m²-day (3-day HRT), about 4 to 5 times higher than those fed with other types of wastewaters. Considering the high ash content in the biomass, the ash-free based biomass productivity was also evaluated. Again, High-TDS industrial WW resulted in the highest ash-free biomass productivities of 977 mg/m²-day (1-day HRT) and 1,219 mg/m²-day (3-day HRT) among different wastewater streams. Between the two HRT levels, however, the biomass productivity did not vary significantly.

Although the RAB and BC reactors used different criteria to quantify the biomass productivity, the above results consistently indicated that a similar trend of algae growth in different types of wastewater streams, i.e., High-TDS industrial WW resulted in the best cell growth while the other three types of wastewater streams led to a similar growth performance. Compared to the algal productivity obtained in High-TDS industrial WW, the limited cell growth in low-TDS industrial WW, Ames WW, and Ames WW+NaCl were probably due to the insufficient nutrients, particularly essential nutrients such as nitrogen and phosphorus in these three wastewater streams (see Table 1).

TDS Removal Performance. The TDS concentrations in the effluent of RAB and BC reactors were monitored during the entire continuous operation period. FIGS. 23A-23D shows the TDS concentrations in influent and effluent of RAB and BC reactors at 3-day HRT conditions. The influent TDS concentrations of these reactors maintained constant during the continuous operation period, ranging from 840 to 12,000 mg/L. For each type of wastewater, the effluent TDS concentrations increased initially and reached the steady state with the culture progressing. Overall, the RAB reactors have lower TDS concentrations than the BC reactors.

A summary of the TDS removal performance in RAB and BC reactors is presented in Table 4. Table 4 shows the TDS removal efficiency (TDS-E, %), the removal rate based on liquid volume (TDS-Rvolume, mg/L-day), and the removal rate based on surface area (TDS-Rsurface, mg/m2-day) of RAB reactor at 1-day HRT (RAB-1), the RAB reactor at 3-day HRT (RAB-3), and the bubble column reactor at 3-day HRT (BC-3), respectively fed with different wastewater sources.

TABLE 4

| TDS removal parameters under different | Algal Reactor-HRT | | |
|---|---|---|---|
| WW sources | RAB-1 | RAB-3 | BC-3 |
| TDS-E (%) | | | |
| Low-TDS industrial WW | 9.10 ± 3.26 | 16.24 ± 8.98 | 4.05 ± 0.17 |
| High-TDS industrial WW | 23.83 ± 3.59 | 27.33 ± 5.09 | 3.37 ± 0.92 |
| Ames WW | 12.39 ± 1.43 | 25.90 ± 8.03 | 8.12 ± 2.06 |
| Ames WW + NaCl | 8.44 ± 1.40 | 14.35 ± 5.12 | 2.99 ± 1.51 |
| TDS-$R_{volume}$ (mg/L-day) | | | |
| Low-TDS industrial WW | 309 ± 38.26 | 183 ± 23.24 | 45.73 ± 2.06 |
| High-TDS industrial WW | 2,783 ± 192 | 1,089 ± 189 | 121 ± 11.12 |
| Ames WW | 101 ± 12.83 | 72.80 ± 23.64 | 22.40 ± 5.60 |
| Ames WW + NaCl | 165 ± 17.43 | 96.37 ± 35.20 | 20.65 ± 14.01 |
| TDS-$R_{surface}$ (mg/m²-day) | | | |
| Low-TDS Industrial WW | 2166 ± 174 | 1,284 ± 100 | n/a |
| High-TDS Industrial WW | 19,530 ± 1,479 | 7,642 ± 52.47 | n/a |
| Ames WW | 707 ± 90.06 | 511 ± 77.18 | n/a |
| Ames WW + NaCl | 1,159 ± 385 | 676 ± 71.46 | n/a |

Overall, TDS removal efficiency (TDS-E) of the RAB reactors was higher than the BC reactors. Among the two HRT levels for the RAB reactors, the longer HRT resulted in higher TDS-E values. Among four types of wastewaters, industrial WW with high TDS led in the highest TDS-E values. The TDS removal rate by the algal culture systems was also evaluated based on the liquid volume (TDS-$R_{volume}$) and attachment surface (TDS-$R_{surface}$). Similar to the trend of TDS-E, TDS-$R_{volume}$ of the RAB reactors was much higher than that of the BC reactor. The industrial WW/high TDS also demonstrated the best TDS removal rate among four different wastewaters. However, contrary to that the trend of TDS-E with HRT, shorter HRT resulted in higher TDS-$R_{volume}$ and TDS-$R_{surface}$ values for the RAB reactors, probably due to the higher TDS mass turnover rate at shorter HRT.

The results indicate that the RAB system was more effective than the suspended algae system for removing TDS from wastewater and was capable of decreasing TDS up to 27% at 3-day of HRT by the RBA reactor (Table 4). Thus, the RAB system can serve as an efficient and environmentally friendly system for TDS removal from wastewater.

Chloride Removal Performance. As chloride is the major ion in all the four wastewater streams tested, the removal performances of this specific TDS species were investigated. The chloride concentrations in influent and effluent of the RAB and BC reactors were monitored. As shown in FIGS. 24A-24D, for all the four wastewater streams, the chloride concentrations in effluent increased initially and reached steady state after 10 to 20 days of operation, depending on the types of the wastewater and reactors. RAB reactors resulted in a lower chloride concentrations in effluent compared to the BC reactor.

The chloride removal performance was further summarized in Table 5. Table 5 shows the chloride removal efficiency (Chloride-E, %), the removal rate based on liquid volume (Chloride-Rvolume, mg/L-day), and the removal rate based on surface area (Chloride-Rsurface, mg/m2-day) of the RAB reactor at 1-day HRT (RAB-1), the RAB rector at 3-day HRT (RAB-3), and the bubble column reactor at 3-day HRT (BC-3), respectively fed with different wastewater sources.

TABLE 5

| Chloride removal parameters under different WW sources | Algal Reactor-HRT | | |
|---|---|---|---|
| | RAB-1 | RAB-3 | BC-3 |
| Chloride-E (%) | | | |
| Low-TDS Industrial WW | 21.21 ± 8.07 | 31.61 ± 9.42 | 13.03 ± 5.71 |
| High-TDS Industrial WW | 27.13 ± 12.20 | 37.32 ± 13.19 | 13.47 ± 5.05 |
| Ames WW | 15.44 ± 1.33 | 34.07 ± 8.98 | 19.42 ± 2.26 |
| Ames WW + NaCl | 15.74 ± 5.54 | 35.39 ± 9.82 | 11.08 ± 1.37 |
| Chloride-$R_{volume}$ (mg/L-day) | | | |
| Low-TDS Industrial WW | 262 ± 24.71 | 133 ± 14.25 | 54.15 ± 24.29 |
| High-TDS Industrial WW | 1,215 ± 310 | 555 ± 63.00 | 195 ± 54.20 |
| Ames WW | 26.01 ± 11.31 | 19.81 ± 2.85 | 11.07 ± 5.93 |
| Ames WW + NaCl | 112 ± 37.36 | 93.28 ± 17.81 | 29.08 ± 4.21 |
| Chloride-$R_{surface}$ (mg/m²-day) | | | |
| Low-TDS Industrial WW | 1,842 ± 174 | 936 ± 100 | n/a |
| High-TDS Industrial WW | 8,526 ± 992 | 3,895 ± 414 | n/a |
| Ames WW | 184 ± 80.02 | 139 ± 20.00 | n/a |
| Ames WW + NaCl | 786 ± 260 | 650 ± 70.05 | n/a |

The trends of the chloride removal performance (removal efficiency and removal rate) were similar to those observed in the TDS. Both chloride removal efficiency and removal rate (volume- and surface-based) of the RAB reactors were higher than those of the BC reactor. Among the two HRT levels tested for the RAB reactors, shorter HRT resulted a lower chloride removal efficiency but a much higher removal rate. Industrial WW with high TDS had the best chloride removal performance than the other three types of wastewaters. The combined results in Tables 4 and 5 indicate that the RAB reactor was more effective than the BC reactor for removing TDS most likely through the predominant chloride.

Figure 25B:
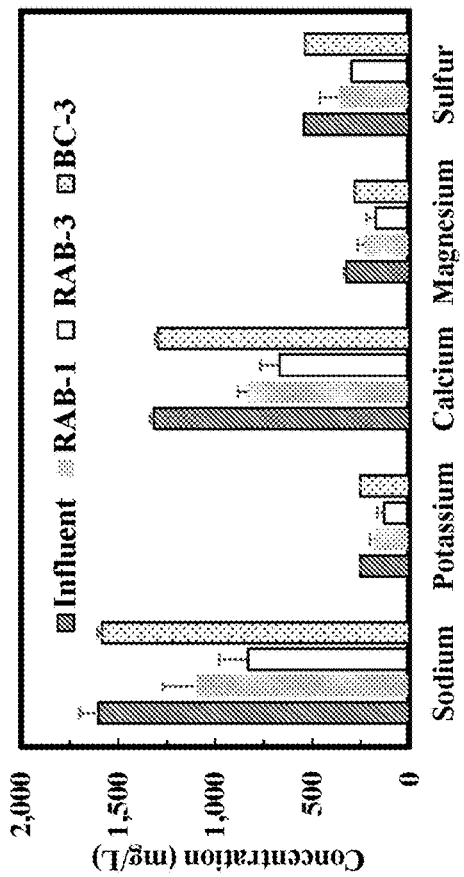
FIG. 25B depicts the concentration of sodium, potassium, calcium, magnesium, and sulfur in the influent and effluent of the continuous operation of RAB and BC reactors fed with a wastewater source of high-TDS industrial WW.
Figure 25D:
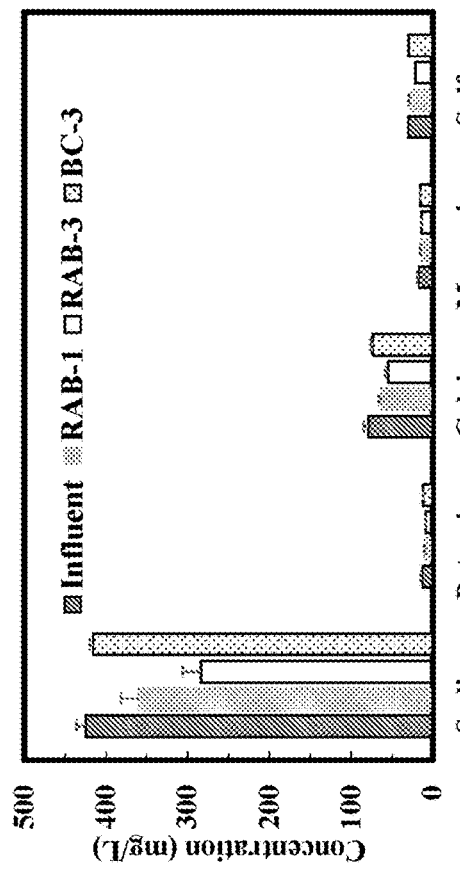
FIG. 25D depicts the concentration of sodium, potassium, calcium, magnesium, and sulfur in the influent and effluent of the continuous operation of RAB and BC reactors fed with a wastewater source of Ames WW+NaCl.
Figure 25A:
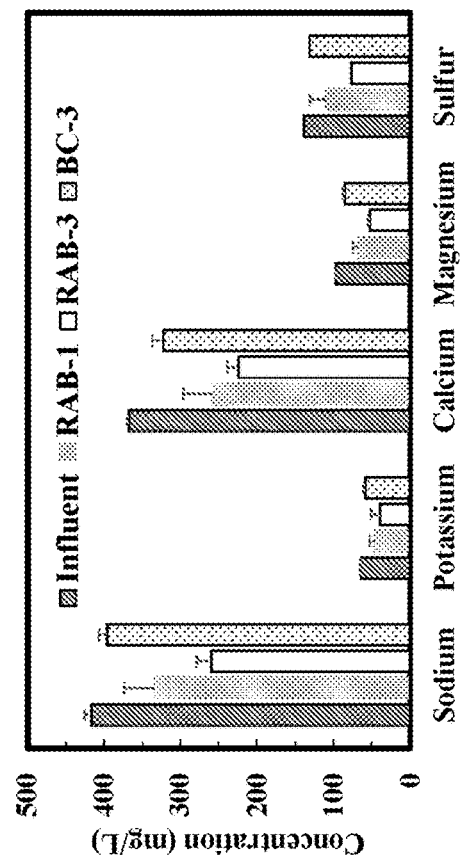
FIG. 25A depicts the concentrations of sodium, potassium, calcium, magnesium, and sulfur in the influent and effluent of the continuous operation of RAB and BC reactors fed with a wastewater (WW) source of low-TDS industrial WW.
Figure 25C:
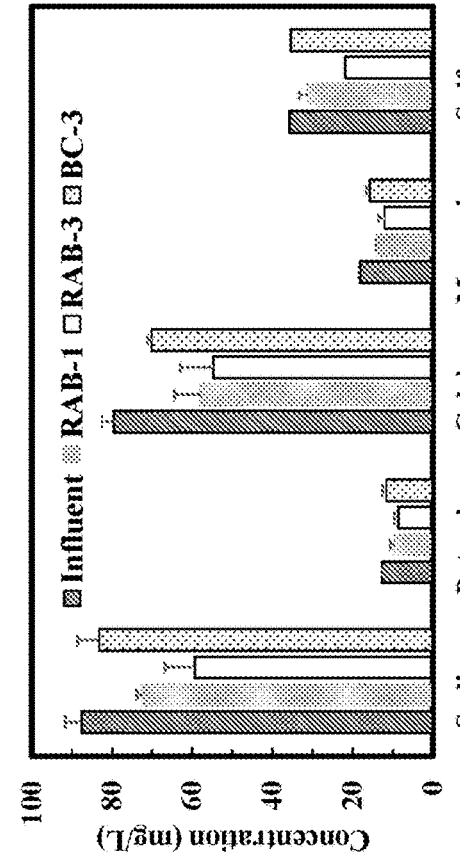
FIG. 25C depicts the concentration of sodium, potassium, calcium, magnesium, and sulfur in the influent and effluent of the continuous operation of RAB and BC reactors fed with a wastewater source of Ames WW.

Removal of Various Ions from Wastewater. In addition to chloride, the removal of other major ionic components such as sodium, potassium, calcium, magnesium and sulfur (Table 1) from wastewater streams was also determined. The concentrations of these metal and non-metal ions in the influent and effluent (at steady state) of the RAB and BC reactors are shown in FIGS. 25A-25D. Among various ions, sodium and calcium were most predominant, followed with sulfur, magnesium, and potassium. For all the wastewaters used, the BC reactors had a limited capability of removing those ions as the influent and effluent concentrations of those elements were almost the same. On the contrary, the RAB reactors demonstrated certain ion removal capacities. The RAB reactors at 3-day HRT (RAB-3) removed more ions than those at 1-day HRT (RAB-1). When industrial WW with high TDS was used as the influent, RAB reactor removed about 50% (3-day HRT) and about 30% (1-day HRT) of these five ions from the influent, while only about 2% of TDS was removed from the BC reactors (FIG. 25B). The industrial WW with high TDS (FIG. 25B) also led to the highest removal efficiency of the ions compared to other three wastewaters (FIGS. 25A, 25C, and 25D).

The algae cultured in the RAB reactors demonstrated a high performance of removing these metals and non-metal ions, especially for the industrial WW with high TDS. This is probably due to the multiple removal mechanisms such as bio-assimilation and/or the physical adsorption by biofilm based EPS.

Ion and EPS Contents of Algal Biomass. The biomass harvested from the algal reactors was analyzed for its ion content. Table 6 shows the ion contents of algal biomass (ash-containing) produced from the RAB reactor at 1-day HRT (RAB-1), the RAB reactor at 3-day HRT (RAB-3), and the bubble column at 3-day HRT (BC-3) fed with different wastewater sources.

TABLE 6

| | Algal Reactor-HRT | | |
|---|---|---|---|
| Compositions | RAB-1 | RAB-3 | BC-3 |
| Low-TDS Industrial WW | | | |
| Sodium (%) | 0.98 ± 0.23 | 0.77 ± 0.28 | 0.68 ± 0.27 |
| Potassium (%) | 0.68 ± 0.05 | 0.70 ± 0.02 | 0.74 ± 0.05 |
| Calcium (%) | 6.60 ± 0.87 | 5.34 ± 0.07 | 5.65 ± 0.95 |
| Magnesium (%) | 1.34 ± 0.33 | 0.86 ± 0.00 | 2.37 ± 0.55 |
| Sulfur (%) | 1.48 ± 0.86 | 0.88 ± 0.17 | 0.74 ± 0.05 |
| High-TDS Industrial WW | | | |
| Sodium (%) | 2.56 ± 0.16 | 2.43 ± 0.04 | 1.61 ± 0.04 |
| Potassium (%) | 0.60 ± 0.12 | 0.72 ± 0.01 | 0.68 ± 0.00 |
| Calcium (%) | 13.54 ± 2.82 | 12.35 ± 0.59 | 9.90 ± 0.36 |
| Magnesium (%) | 3.08 ± 0.25 | 2.02 ± 0.25 | 7.33 ± 0.20 |
| Sulfur (%) | 5.81 ± 0.30 | 4.57 ± 0.17 | 0.48 ± 0.00 |
| Ames WW | | | |
| Sodium (%) | 0.26 ± 0.05 | 0.26 ± 0.01 | 0.15 ± 0.03 |
| Potassium (%) | 0.69 ± 0.08 | 0.68 ± 0.08 | 0.70 ± 0.24 |
| Calcium (%) | 3.67 ± 0.00 | 3.76 ± 0.00 | 5.38 ± 1.07 |
| Magnesium (%) | 0.43 ± 0.10 | 0.38 ± 0.15 | 0.45 ± 0.11 |
| Sulfur (%) | 0.75 ± 0.05 | 0.72 ± 0.07 | 0.84 ± 0.07 |
| Ames WW + NaCl | | | |
| Sodium (%) | 1.06 ± 0.25 | 0.79 ± 0.06 | 0.73 ± 0.09 |
| Potassium (%) | 0.67 ± 0.10 | 0.75 ± 0.04 | 0.77 ± 0.00 |
| Calcium (%) | 6.92 ± 0.00 | 4.41 ± 0.00 | 5.72 ± 0.09 |
| Magnesium (%) | 0.31 ± 0.10 | 0.51 ± 0.20 | 0.31 ± 0.00 |
| Sulfur (%) | 0.69 ± 0.02 | 0.64 ± 0.02 | 1.15 ± 0.08 |

Calcium was the most predominant ion in the biomass followed with sulfur, magnesium, sodium, and potassium. Potassium content in biomass maintained at a relatively constant level (e.g., 0.6 to 0.7%) throughout all the experimental conditions, while calcium, magnesium, sodium and sulfur contents were altered and matched with the concentration level of these ions in wastewaters. The stable potassium content across different biomass samples indicated algal cells may have the capability of adjusting potassium adsorption to maintain a balanced intracellular and extracellular osmosis. The results from sulfur removal from different wastewaters (FIGS. 25A-25D) indicate that biofilm algae in the RAB reactors can absorb more sulfur than the suspended algae in the BC reactors.

In algal biofilm reactors, microalgae cells excrete EPS into their immediate environment to form a hydrated biofilm matrix, which was believed to help to adsorb TDS from wastewater; therefore, the algal biomass was further characterized for the EPS content of the algal biomass. Polysaccharides and proteins are two major components in algal EPS. Table 7 shows the EPS contents of algal biomass (ash-free dry weight (AFDW)) produced from RAB at 1-day HRT (RAB-1), RAB at 3-day HRT (RAB-3), and bubble column at 3-day HRT (BC-3) fed with different wastewater sources.

TABLE 7

| EPS contents | Algal Reactor-HRT | | |
|---|---|---|---|
| (mg/g AFDW) | RAB-1 | RAB-3 | BC-3 |
| Low-TDS Industrial WW | | | |
| Protein in EPS | 3.28 ± 0.20 | 2.56 ± 0.14 | 5.15 ± 0.17 |
| Polysaccharide in EPS | 95.09 ± 3.51 | 156.23 ± 10.02 | 17.56 ± 5.40 |
| Total EPS | 98.37 | 158.79 | 22.71 |
| High-TDS Industrial WW | | | |
| Protein in EPS | 8.51 ± 0.26 | 13.48 ± 1.87 | 13.05 ± 1.93 |
| Polysaccharide in EPS | 53.72 ± 6.11 | 71.28 ± 7.36 | 50.94 ± 1.67 |
| Total EPS | 62.23 | 84.76 | 63.99 |
| Ames WW | | | |
| Protein in EPS | 18.01 ± 2.05 | 20.84 ± 1.28 | 23.20 ± 0.84 |
| Polysaccharide in EPS | 116.95 ± 0.63 | 135.27 ± 4.92 | 80.99 ± 7.24 |
| Total EPS | 134.95 | 156.11 | 104.18 |
| Ames WW + NaCl | | | |
| Protein in EPS | 7.57 ± 0.71 | 8.79 ± 1.01 | 4.92 ± 0.18 |
| Polysaccharide in EPS | 144.85 ± 1.38 | 148.24 ± 17.05 | 75.41 ± 006 |
| Total EPS | 152.41 | 157.03 | 80.33 |

Throughout all the biomass samples, the polysaccharide content was much higher than the proteins. The EPS protein contents in RAB and BC biomass were similar, while the EPS polysaccharide content was higher in RAB derived biomass than those in BC biomass. As a result, RAB biomass contained a higher total EPS than the BC derived biomass. Between the two HRT levels in the RAB reactors, the 3-day HRT resulted in a higher EPS polysaccharide than the 3-day HRT. The EPS polysaccharides in the RAB biofilm biomass are considered the major contributor for adsorbing TDS ions.

Overall, the results demonstrate that the RAB reactors can efficiently remove TDS from wastewater and be used as a sustainable and environmentally friendly method for wastewater remediation. The efficiencies of removing TDS, chloride, and other ions of the RAB reactors were higher than those of the suspended algal culture system and depended on the HRT. The EPS content of the algal biofilm, particularly the protein and polysaccharides in EPS, was higher in RAB reactors than in suspended culture systems and was responsible for the high TDS removal efficiencies.

Example 2

Studies on TDS removal using a RAB system were conducted at the Metropolitan Water Reclamation District of Greater Chicago's O'Brien Water Reclamation Plant. Two heights of the belts of the RAB system were used, 6-ft tall and 3-ft tall, against a standard raceway pond as a control. The wastewater was a stream of supernatant from gravity thickening of sludge. Ash content of the biomass produced was used as a surrogate for TDS removal, as ash left after combustion of algal biomass consists of mostly salts (metal ions such as Ca, Mg, Cu, Ni, Zn, Fe, Na, K, etc. and anions such as Cl, $SO_4$, $PO_4$, $CO_3$, etc.). These constituents are either absorbed in algal cells from the wastewater or are adsorbed on surface of algal cell walls and/or on to the EPS produced by algal cells. Only a small proportion of constituents, such as dissolved organic compounds, which are considered a part of TDS, are lost during combustion process used to quantify ash content in algal biomass. The results are shown in Table 8.

TABLE 8

| | Control Raceway | 3-ft RAB | 6-ft RAB |
|---|---|---|---|
| Ash content (%) | 11.4 ± 3.2 | 16.7 ± 2.9 | 20.8 ± 3.7 |

The results showed that the ash content of the algal biomass from the 6-ft RAB system were greater than the ash content of algal biomass from the 3-ft RAB. Further, the ash content of the algal biomass from both of the RAB systems were greater than the ash content of the algal biomass from the control raceway pond. Thus, the results showed that algal biofilms growing on RAB system, when moved outside of the water column and exposed to a gaseous environment, are capable of removing greater amounts of TDS from wastewater than the algae growing in suspension in the water column as in traditional raceway ponds. These Examples and results are also discussed in Peng, Juan, et al., "Removal of total dissolved solids from wastewater using a revolving algal biofilm reactor," Water Environment Research (2019), which is incorporated by reference herein in its entirety.

In various embodiments disclosed herein, a single component can be replaced by multiple components and multiple components can be replaced by a single component to perform a given function or functions. Except where such substitution would not be operative, such substitution is within the intended scope of the embodiments.

Some of the figures can include a flow diagram. Although such figures can include a particular logic flow, it can be appreciated that the logic flow merely provides an exemplary implementation of the general functionality. Further, the logic flow does not necessarily have to be executed in the order presented unless otherwise indicated. In addition, the logic flow can be implemented by a hardware element, a software element executed by a computer, a firmware element embedded in hardware, or any combination thereof.

The foregoing description of embodiments and examples has been presented for purposes of illustration and description. It is not intended to be exhaustive or limiting to the forms described. Numerous modifications are possible in light of the above teachings. Some of those modifications have been discussed, and others will be understood by those skilled in the art. The embodiments were chosen and described in order to best illustrate principles of various embodiments as are suited to particular uses contemplated. The scope is, of course, not limited to the examples set forth herein, but can be employed in any number of applications and equivalent devices by those of ordinary skill in the art. Rather it is hereby intended the scope of the invention to be defined by the claims appended hereto.

We claim:

1. A method of reducing total dissolved solids in wastewater comprising:
providing an algal biofilm, the algal biofilm comprising a material configured for growth and attachment of a defined mass of algae;
providing a fluid reservoir containing a portion of wastewater fluid;
moving the algal biofilm through the portion of wastewater fluid in the fluid reservoir;
providing a stressor to algae in the algal biofilm to trigger a defense mechanism of the defined mass of algae such that a first amount of an extracellular polymeric substance is produced, wherein the stressor comprises exposing the algal biofilm to a first liquid phase and a second gas phase, and wherein the second gas phase comprises rotating the algal biofilm out of the first liquid phase to expose the algal biofilm to ambient air; and
removing a portion of total dissolved solids in the portion of wastewater fluid with the extracellular polymeric substance.

2. The method of claim 1, wherein the stressor is biotic or abiotic.

3. The method of claim 1, wherein the stressor is selected from the group consisting of increasing the pH of the algal biofilm, decreasing the pH of the algal biofilm, increasing the temperature of the algal biofilm, decreasing the temperature of the algal biofilm, modulating the temperature of the algal biofilm, adjusting an amount of light applied to the algal biofilm, adjusting a wavelength of the light applied to the algal biofilm, and combinations thereof.

4. The method of claim 1, wherein the extracellular polymeric substance comprises proteins and polysaccharides.

5. The method of claim 1, further comprising an algal growth system, the algal growth system comprising:
(a) a vertical reactor configured to retain the algal biofilm;
(b) a shaft, wherein the shaft is associated with and supports the algal biofilm; and
(c) a drive motor, the drive motor being coupled with the shaft such that the algal biofilm is selectively actuated.

6. The method of claim 1, further comprising harvesting the algae from the algal biofilm.

7. The method of claim 1, further comprising precipitating salts from the portion of wastewater fluid in the fluid reservoir, wherein removing a portion of total dissolved solids in the portion of wastewater fluid further comprises removing at least a portion of precipitated salts.

8. The method of claim 1, further comprising providing a second amount of extracellular polymeric substance created by the defined mass of algae.

9. A method of reducing total dissolved solids in wastewater comprising the steps of:
providing an algal growth system comprising:
(a) a vertical reactor comprising;
(i) a flexible sheet material, the flexible sheet material being configured to facilitate growth and attachment of algae;
(ii) a shaft, wherein the shaft is associated with and supports the flexible sheet material; and
(iii) a drive motor, the drive motor being coupled with the shaft such that the flexible sheet material is selectively actuated;
(b) a fluid reservoir, wherein the flexible sheet material is configured to pass through the fluid reservoir during operation of the algal growth system, the vertical reactor being positioned at least partially within the fluid reservoir; and
(c) a portion of wastewater, wherein the portion of wastewater is retained within the fluid reservoir and includes an amount of total dissolved solids;
rotating the flexible sheet material of the algal growth system through the portion of wastewater retained in the fluid reservoir in a first liquid phase;
rotating the flexible sheet material of the algal growth system through a gas in a second gas phase, wherein the second gas phase comprises rotating the flexible sheet material out of the first liquid phase to expose the flexible sheet material to ambient air to trigger a defense mechanism of the defined mass of algae such that a first amount of an extracellular polymeric substance is produced; and
harvesting the algae from the flexible sheet material; and
wherein stimulating the production of the extracellular polymeric substance reduces the amount of total dissolved solids in the portion of wastewater.

10. The method of claim 9, wherein rotation of the flexible sheet material of the algal growth system through the gas is a first stressor, and wherein the method further comprises providing a second stressor.

11. The method of claim 9, further comprising providing a plurality of algal growth systems to decrease the amount of total dissolved solids in a water system.

12. The method of claim 9, further comprising precipitating salts from the portion of wastewater fluid in the fluid reservoir, wherein removing a portion of total dissolved solids in the portion of wastewater fluid further comprises removing at least a portion of precipitated salts.

13. A method of reducing total dissolved solids in wastewater comprising:
providing an algal biofilm, the algal biofilm comprising a material configured for the growth and attachment of a defined mass of algae;
providing a fluid reservoir containing a portion of wastewater fluid;
moving the algal biofilm including the defined mass of algae through the portion of wastewater fluid in the fluid reservoir;
providing a stressor to the defined mass of algae in the algal biofilm to affect the defined mass of algae such that a first amount of extracellular polymeric substance is created by the defined mass of algae, wherein the stressor comprises exposing the algal biofilm to a first liquid phase and a second gas phase, wherein the second gas phase comprises rotating the algal biofilm out of the first liquid phase to expose the algal biofilm to ambient air; and
removing a portion of total dissolved solids in the portion of the wastewater fluid.

14. The method of claim 13, wherein the stressor is biotic or abiotic.

15. The method of claim 13, wherein the stressor is selected from the group consisting of increasing the pH of the algal biofilm, decreasing the pH of the algal biofilm, increasing the temperature of the algal biofilm, decreasing the temperature of the algal biofilm, modulating the temperature of the algal biofilm, adjusting an amount of light applied to the algal biofilm, adjusting a wavelength of the light applied to the algal biofilm, and combinations thereof.

16. The method of claim 13, wherein the extracellular polymeric substance comprises proteins and polysaccharides.

17. The method of claim 13, further comprising an algal growth system, the algal growth system comprising:
  (a) a vertical reactor configured to retain the algal biofilm;
  (b) a shaft, wherein the shaft is associated with and supports the algal biofilm; and
  (c) a drive motor, the drive motor being coupled with the shaft such that the algal biofilm is selectively actuated.

18. The method of claim 13, further comprising harvesting the algae from the algal biofilm.

* * * * *